(12) United States Patent
Ferracane et al.

(10) Patent No.: US 12,181,456 B2
(45) Date of Patent: Dec. 31, 2024

(54) THERMOPLASTIC FILMS AND BAGS WITH MALODOR PARTICLE BASED ODOR CONTROL AND METHODS OF MAKING THE SAME

(71) Applicant: THE GLAD PRODUCTS COMPANY, Oakland, CA (US)

(72) Inventors: Dean Ferracane, Willowbrook, IL (US); Jessica Greer, Willowbrook, IL (US); Jeffrey S. Stiglic, Willowbrook, IL (US); Robert T. Dorsey, Willowbrook, IL (US)

(73) Assignee: THE GLAD PRODUCTS COMPANY, Oakland, CA (US)

( * ) Notice: Subject to any disclaimer, the term of this patent is extended or adjusted under 35 U.S.C. 154(b) by 566 days.

(21) Appl. No.: 17/280,996

(22) PCT Filed: Sep. 18, 2019

(86) PCT No.: PCT/US2019/051714
§ 371 (c)(1),
(2) Date: Mar. 29, 2021

(87) PCT Pub. No.: WO2020/072202
PCT Pub. Date: Apr. 9, 2020

(65) Prior Publication Data
US 2021/0339510 A1    Nov. 4, 2021

Related U.S. Application Data

(60) Provisional application No. 62/740,303, filed on Oct. 2, 2018.

(51) Int. Cl.
*G01N 31/22* (2006.01)
*A61L 9/01* (2006.01)
(Continued)

(52) U.S. Cl.
CPC .............. *G01N 31/225* (2013.01); *A61L 9/01* (2013.01); *A61L 9/012* (2013.01); *B32B 1/00* (2013.01);
(Continued)

(58) Field of Classification Search
CPC .......... A61L 9/01; A61L 9/012; G01N 31/225
See application file for complete search history.

(56) References Cited

U.S. PATENT DOCUMENTS 4,425,321 A * 1/1984 Jacquet .................. C07C 61/22
424/47
2003/0215417 A1 11/2003 Uchiyama et al.
(Continued)

OTHER PUBLICATIONS

Office Action as received in Chinese application 201980079071.6 dated Feb. 24, 2023.
(Continued)

*Primary Examiner* — Derek J Battisti
(74) *Attorney, Agent, or Firm* — Keller Preece PLLC

(57) ABSTRACT

The present disclosure relates to a thermoplastic film that includes a layer of thermoplastic material and an encapsulated odor control component. The encapsulated odor control component can include an odor-control active encapsulated within an odor-control encapsulant. Additionally, the encapsulated odor control component can be configured to release the odor-control active from the encapsulant when exposed to malodor particles. The thermoplastic film can further include a color indicator that changes color to indicate performance of the encapsulated odor control component. For example, the color indicator can change from a first color to a second color based, at least in part, on the release of the odor-control active.

20 Claims, 14 Drawing Sheets

(51) Int. Cl.
   *A61L 9/012* (2006.01)
   *B32B 1/00* (2024.01)
   *B32B 7/027* (2019.01)
   *B32B 27/08* (2006.01)
   *B65D 30/08* (2006.01)
   *B65D 33/00* (2006.01)
   *G01N 21/78* (2006.01)

(52) U.S. Cl.
   CPC .............. *B32B 7/027* (2019.01); *B32B 27/08* (2013.01); *B65D 31/02* (2013.01); *B65D 33/004* (2013.01); *G01N 21/78* (2013.01); *G01N 31/22* (2013.01); *G01N 31/222* (2013.01); *B32B 2307/758* (2013.01); *B32B 2439/06* (2013.01)

(56) References Cited

U.S. PATENT DOCUMENTS

| | | | |
|---|---|---|---|
| 2005/0112085 A1* | 5/2005 | MacDonald | B01J 20/3204 424/76.1 |
| 2006/0120633 A1* | 6/2006 | Goldenberg | B65D 31/02 383/63 |
| 2009/0067760 A1* | 3/2009 | Shelley | B65D 81/28 264/238 |
| 2009/0175564 A1* | 7/2009 | Broering | B65F 1/0006 383/105 |
| 2012/0145191 A1 | 6/2012 | Williams et al. | |
| 2017/0008261 A1* | 1/2017 | Jean-Mary | B32B 27/08 |
| 2018/0118415 A1* | 5/2018 | Jean-Mary | B31B 70/8134 |
| 2019/0217994 A1* | 7/2019 | Duruduygu | B65D 33/01 |
| 2020/0103383 A1* | 4/2020 | Ferracane | G01N 31/22 |
| 2021/0043658 A1 | 2/2021 | Song | |

OTHER PUBLICATIONS

International Search Report as received in PCT/US2019/051714 dated Dec. 4, 2019.

Office Action as received in Chinese application 201980079071.6 dated Sep. 20, 2022.

Examination Report as received in Australian application 2019354591 dated Aug. 6, 2024.

\* cited by examiner

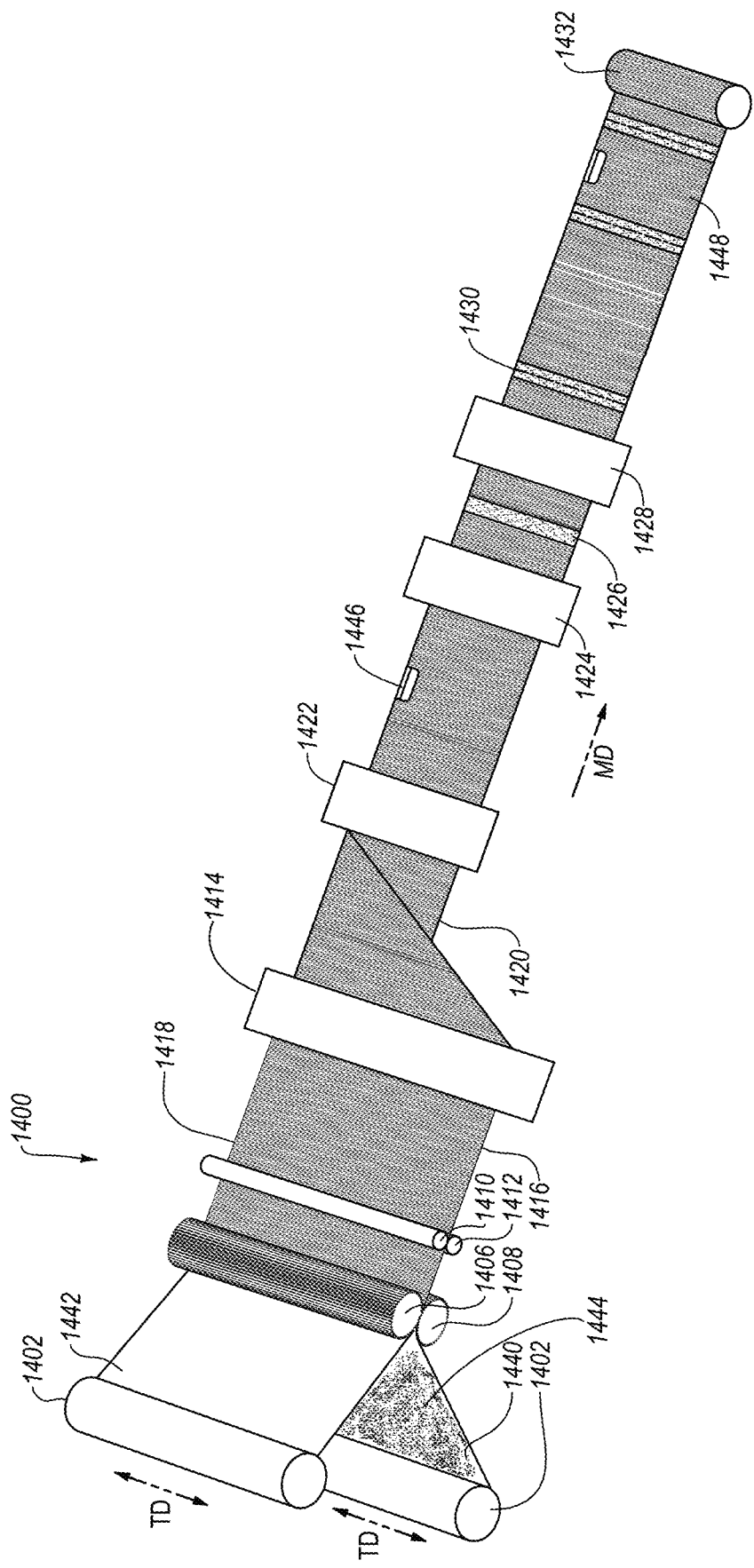

THERMOPLASTIC FILMS AND BAGS WITH MALODOR PARTICLE BASED ODOR CONTROL AND METHODS OF MAKING THE SAME

CROSS-REFERENCE TO RELATED APPLICATIONS

This application is a 35 U.S.C. 371 national phase of PCT International Application No. US2019/51714, filed on Sep. 18, 2019, which claims the benefit of and priority to U.S. Provisional Application No. 62/740,303, filed Oct. 2, 2018 and entitled: THERMOPLASTIC FILMS AND BAGS WITH MALODOR PARTICLE BASED ODOR CONTROL AND METHODS OF MAKING THE SAME. The contents of the above-referenced applications are hereby incorporated by reference in their entirety.

BACKGROUND

Thermoplastic films are a common component in various commercial and consumer products. For example, grocery bags, trash bags, sacks, and packaging materials are products that are commonly made from thermoplastic films. Additionally, feminine hygiene products, baby diapers, adult incontinence products, and many other products include thermoplastic films to one extent or another.

In regard to trash bags formed from thermoplastic films, controlling malodors from materials placed in the trash bags (e.g., trash) is a significant concern. As a result, trash bags are often scented to help mask (e.g., hide) the malodors that escape from the bag (e.g., permeate through the layers of the bag or escape through the top of the bag during consumer use). The trash bags are typically "scented" by coating one or more sides (e.g., the interior or exterior sides) with a fragrance or by coextruding the fragrance with the thermoplastic film forming the trash bag (i.e., embedding the fragrance as an additive into the thermoplastic film during the extrusion process).

Alternatively, or additionally, manufactures may add a neutralizing component to the trash bag (e.g., by coating one or more sides of the trash bag with the neutralizing component or by coextruding the neutralizing component with the thermoplastic film forming the trash bag) to neutralize any malodors within the bag. However, neutralizing components (e.g., solid, non-volatile neutralizing components, such as baking soda) typically require direct contact with the source of a malodor (i.e., the trash) before they can neutralize the malodor itself. Therefore, such neutralizing components typically fail to neutralize malodors produced by trash positioned within the center of the trash bag (i.e., not touching any of the sides).

Another disadvantage of conventional malodor-controlling components is that their effectiveness diminishes over a relatively short period of time. For example, a consumer may place a trash bag within a trash container, but not actually place trash into the container for a period of time. During this period of time, any malodor control components (e.g., a volatile fragrance or odor neutralizer) can begin losing potency. By the time trash is placed in the trash bag, the effectiveness of the fragrance may have already diminished such that the fragrance does not help the odor of the trash.

Further, many malodor-controlling components are limited in their functionality, which limits their usefulness in controlling malodors. For example, many non-volatile malodor-controlling components disposed on the surface of a trash bag may remain effective for long periods of time (as many such non-volatile components only function when in direct contact with a malodor source); however, such non-volatile components often fail to control odor emanating from trash in the center of the bag. On the other hand, while many volatile malodor-controlling components may be capable of controlling odors emanating from sources that don't contact the surface of the trash bag, such volatile components typically diminish whether trash is present or not. Therefore, use of these volatile components risks dissipation before there is a need to control any malodor.

Accordingly, there are a number of considerations to be made in thermoplastic films and controlling odors with thermoplastic films.

SUMMARY

One or more embodiments of the present invention provide benefits and/or solve one or more of the foregoing or other problems in the art with thermoplastic films and bags that include an encapsulated odor control component that operates to control odor based on the presence of malodor particles. For example, in one or more embodiments, a thermoplastic film includes a layer of thermoplastic material and an encapsulated odor control component. The encapsulated odor control component can include an odor-control active encapsulated within an odor-control encapsulant. Additionally, the encapsulated odor control component can be configured to release the odor-control active from the encapsulant when exposed to malodor particles. As such, the encapsulated odor control component releases little, to no, odor-control active when not in the presence of malodor. Furthermore, as a malodor source is introduced, the encapsulated odor control component is triggered to release the odor-control active. In one or more embodiments, the encapsulated odor control component releases an amount of odor-control active based on the amount of malodor components present. In one or more embodiments, the thermoplastic film further includes a color indicator that changes color to indicate performance of the encapsulated odor control component. For example, the color indicator can change from a first color to a second color based, at least in part, on the release of the odor-control active.

One or more embodiments include a film comprising a first layer of thermoplastic material and an encapsulated odor control component comprising an odor-control active encapsulated within an odor-control encapsulant. The encapsulated odor control component is configured to release the odor-control active when exposed to malodor particles.

One or more further embodiments include a thermoplastic bag comprising a first sidewall and a second sidewall opposite the first sidewall and joined with the first sidewall along a first side edge, an opposite second side edge, and a bottom edge. The thermoplastic bag also includes an encapsulated odor control component comprising an odor-control active encapsulated within an odor-control encapsulant. The encapsulated odor control component is configured to release the odor-control active to neutralize malodor particles.

Additionally, one or more embodiments include a method of manufacturing thermoplastic bags having odor control. The method involves providing a thermoplastic film; and providing an encapsulated odor control component. The encapsulated odor control component comprises an odor-control active encapsulated within an odor-control encapsulant and is configured to release the odor-control active when exposed to malodor particles. The method also involves forming the thermoplastic film into a bag.

Additional features and advantages of exemplary implementations of the present invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above recited and other advantages and features of the present disclosure can be obtained, a more particular description of the present disclosure briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. Understanding that these drawings depict only typical embodiments of the present disclosure and are not therefore to be considered to be limiting of its scope, the present disclosure will be described and explained with additional specificity and detail through the use of the accompanying drawings in which:

FIG. 14 illustrates a schematic diagram of another manufacturing process for producing thermoplastic bags having an odor control component in accordance with one or more embodiments.

DETAILED DESCRIPTION

Figure 1:
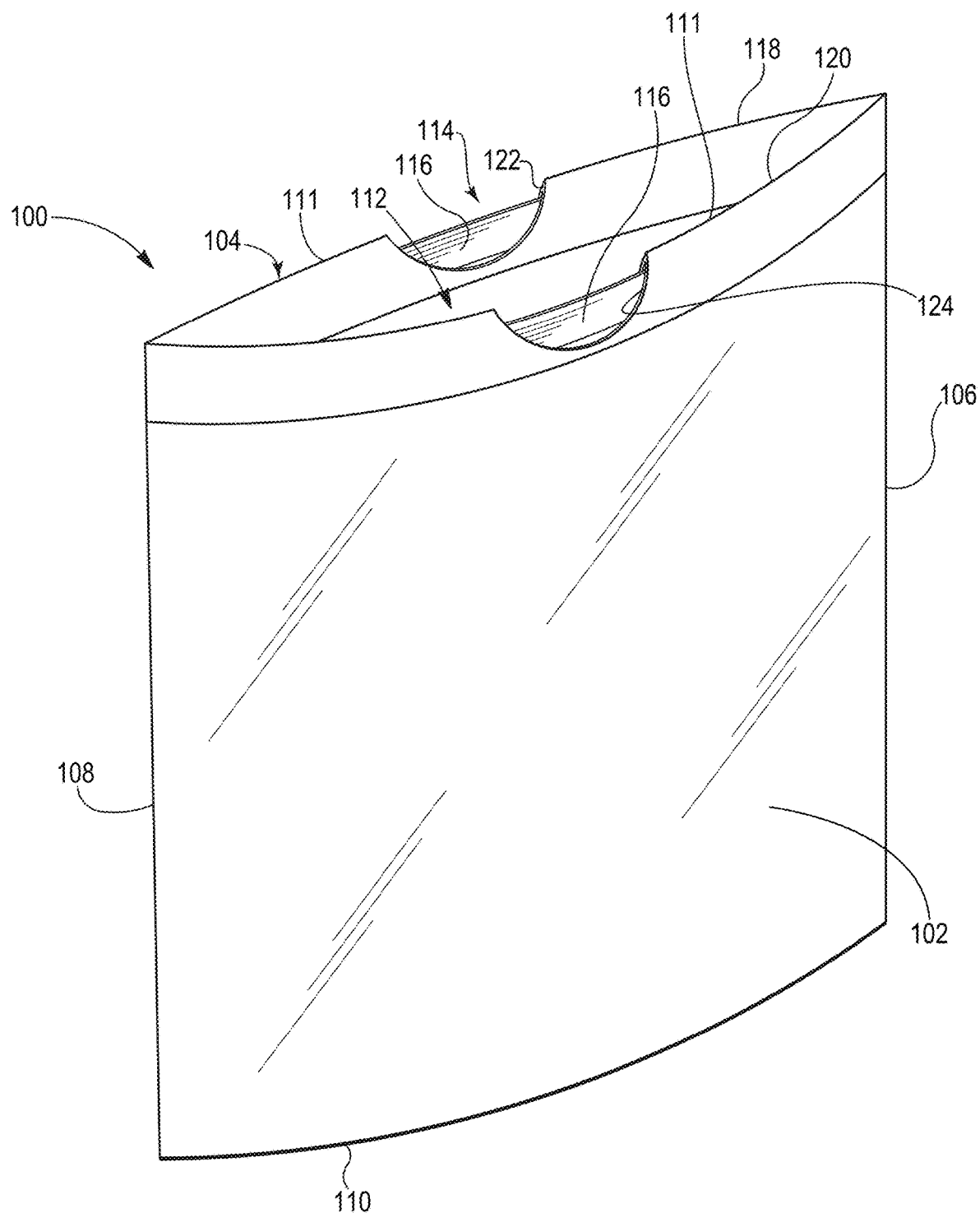
FIG. 1 shows a perspective view of a thermoplastic bag in accordance with one or more embodiments.

One or more embodiments of the present disclosure include an encapsulated odor control component that operates to control odor based on the presence of malodor particles. For example, in one or more embodiments, a thermoplastic film or bag comprises an odor-control active within an odor-control encapsulant. The encapsulated odor control component is configured to release the odor-control active from the encapsulant when exposed to malodor particles. For example, the encapsulated odor control component releases little, to no, odor-control active when not in the presence of malodor. On the other hand, as a malodor source is introduced, the encapsulated odor control component is triggered to release the odor-control active. In one or more embodiments, the encapsulated odor control component releases an amount of odor-control active based on the amount of malodor components present.

In one or more embodiments, the encapsulated odor control component is coextruded with the thermoplastic material so that the encapsulated odor control component is embedded into the material itself. In some embodiments, the encapsulated odor control component is applied to the thermoplastic material after extrusion (e.g., using a liquid or a powder application). For example, the encapsulated odor control component can be disposed onto a surface of the thermoplastic material (e.g., in a pattern—such as a strip, a series of dots, or other predetermined pattern—or as a complete layer covering the surface), within a hem of the thermoplastic material, or between a first layer and a second layer of the thermoplastic material.

The odor-control active within the odor-control encapsulant can include one or more volatile fragrances and/or odor control agents. For example, the odor-control active can include one or more of desiccant materials, antimicrobial agents, deodorizing agents, neutralizing agents, trapping/adsorbing agents, oxidizing agents, absorbing agents, or functional nanoparticles. As a result, in one or more embodiments, the odor control component reduces an amount of malodor molecules that permeate through the thermoplastic film or escape through an opening of the film (e.g., the top of a trash bag uncovered during consumer use), masks malodor molecules, and/or otherwise neutralizes malodor.

Some embodiments include an odor-control active that at least partially absorbs and/or traps malodor molecules. In other words, the odor control component can "catch" the malodor molecules. By absorbing and/or trapping the malodor molecules, the odor control component can help reduce or prevent the malodor molecules from spreading or leaving a product.

Further, as mentioned above, in one or more embodiments, the encapsulated odor control component is configured to release an odor-control active from an odor-control encapsulant when exposed to malodor particles. In some embodiments, the encapsulated odor control component is configured to release the odor-control active based on the chemical structure of the malodor particles. To illustrate, some embodiments involve configuring the encapsulated odor control component to release the odor-control active based on a chemical structure that provides the malodor particles with a particular pH level. For example, the encapsulated odor control component can be configured to release the odor-control active only when exposed to particles having a specific pH level (e.g., 6.5) or a pH level within a range of predetermined pH levels (e.g., 5.0-6.5 inclusive). Consequently, in one or more embodiments, the encapsulated odor control component does not require direct contact with the source of the malodor to release the odor-control active. This significant improvement allows the thermoplastic bag or film of which the encapsulated odor control component is a part to control odor more comprehensively. Additionally, this improvement enables the encapsulated odor control component to perform more efficiently while disposed on locations of the thermoplastic material that do not come in direct contact with malodor sources, such as between layers of thermoplastic material (or, for bags, between layers of film). Because the encapsulated odor control component releases the odor-control active when exposed to malodor particles, the component can simultaneously maintain its effectiveness over long periods of time.

One or more embodiments include multiple encapsulated odor control components triggered to release odor-control actives when exposed to different malodor particles. For example, a sidewall of a thermoplastic bag can include a first strip of a first encapsulated odor control component and a second strip of a second encapsulated odor control component. The first encapsulated odor control component can be configured to release a first odor-control active when exposed to malodor particles from a first set of malodor particles (e.g., malodor particles having a first pH value or a pH value within a first range of pH values). And the second encapsulated odor control component can be configured to release a second odor-control active when exposed to malodor particles from a second set of malodor particles (e.g., malodor particles having a second pH value or a pH value within a second range of pH values). Sill further embodiments can include more than two different encapsulated odor control components.

Additionally, as mentioned above, one or more embodiments further include a color indicator that changes from a first color to a second color based, at least in part, on the release of the odor-control active to indicate performance of the encapsulated odor control component. For example, in some embodiments, the rate of color change is based, at least partly, on a pH level of the odor-control active. To illustrate, the rate of color change can increase as a pH level of the odor-control active decreases (i.e., becomes more acidic). Accordingly, the odor-control active can be engineered with a pH level that causes a desired rate of color change.

As illustrated by the foregoing discussion, the present disclosure utilizes a variety of terms to describe features and benefits of one or more embodiments. Additional detail is now provided regarding the meaning of these terms.

As used herein, the terms "encapsulated odor control component" and "odor control component" refer to a structure or compound that includes an odor-control encapsulant and an odor-control active.

As used herein, the term "odor-control encapsulant" refers to a composition capable of, at least partially, encapsulating another composition (i.e., the odor-control active). In particular, an odor-control encapsulant can bond to, or enclose, an odor-control active. For example, the odor-control encapsulant can include a shell or matrix composition that surrounds the odor-control active. In one or more embodiments, the odor-control encapsulant is configured to release the odor-control active in response to a trigger (e.g., the presence of malodor particles). For example, the odor-control encapsulant can be configured to release the odor-control active in response to the presence of particles/materials having sulfide chemistries, nitrogen chemistries, aldehydes, ketones, ester, or other malodor particles.

As non-limiting examples, the odor-control encapsulant can comprise a crystalline lattice composed of basic material that breaks down in the presence of a volatile fatty acid (or other low pH malodors) due to acid-base reactions, releasing the odor-control active. As another non-limiting example, the odor-control encapsulant can include a flexible matrix (e.g., a matrix created with polymer chains) that encapsulates both the odor-control active and another material, such as a transition metal particle. The other material can react with a malodor (e.g., thiol or mercaptan), when present, relaxing the walls of the matrix and allowing the odor-control active to be released. As a further non-limiting example, the odor control component can comprise magnesium intercalated bleach (a.k.a. "MIB") as disclosed by U.S. Pat. No. 9,040,475, the contents of which are hereby incorporated herein by reference in their entirety.

In one or more embodiments, the odor-control encapsulant is configured to retain (e.g., not release) the odor-control active in the absence of the presence of malodor particles. Along related lines, the odor-control encapsulant can be configured to release the odor-control active in the presence of malodor particles. More particularly, the odor-control encapsulant can release the odor-control active at a rate proportional to the rate of exposure of the odor-control encapsulant to malodor particles. In other words, exposure of a small amount or rate of malodor particles can cause the odor-control encapsulant to release a proportionally small amount or rate of odor-control active. One will appreciate that this can help ensure that a large amount or all of the odor-control active is not released in response to an initial or small amount of malodor particles.

Additionally, the odor-control encapsulant can be configured to release the odor-control active in response to vapor phase contact with malodor particles (i.e., the odor-control encapsulant need not touch the malodor source). In alternative embodiments, the odor-control encapsulant can be configured to release the odor-control active in response to direct physical contact with the malodor source.

As used herein, the term "odor-control active" refers to a composition that effects (e.g., changes and/or masks) odors in at least one manner. For example, the odor-control active can absorb (e.g., foul smell odors) and/or may include fragrance materials. Furthermore, the odor-control active can mask (e.g., cover up) and/or neutralize malodors. As used herein the term "neutralize" or any of its derivative terms refers to an ability of a compound or product to reduce or eliminate malodorous compounds. Odor neutralization may be partial, affecting only some of the malodorous compounds in a given context, or affecting only a portion of a malodorous compound. A malodorous compound may be neutralized by chemical reaction resulting in a new chemical entity, by sequestration, by chelation, by association, or by any other interaction rendering the malodorous compound less malodourous or non-malodorous.

For example, the odor-control active can include one or more gaseous, liquid, colloidal suspension, and/or solid substances. In one or more embodiments, the odor-control active includes a volatile fragrance material (i.e., a fragrance material capable of being transported to the olfactory system). For example, the odor-control active can include top, middle, and/or bottom notes of a fragrance composed of aromatic materials and other functional groups (e.g., ketones, aldehydes, alcohols, etc.). As used herein the term "fragrance" refers to any mixture or composition comprising one or more perfume raw materials with or without one or more carrier solvents configured to emit a pleasant odor.

In one or more embodiments, the odor-control active comprises functional perfume raw materials (e.g., neutralizing chemistries—such as reactive aldehydes—or perceptual modifiers—such as receptor blockers). As used herein the term "perfume" refers to a compound utilized for its appealing odor. Compounds may have a pleasing odor without being used as a perfume in the context of this disclosure.

In further embodiments, the odor-control active comprises one or more neutralizing agents. For example, in some embodiments, the odor-control active includes oxidizing chemistries (e.g., peroxides, hypochlorous acid, chlorine, ozone, sodium perborate, etc.).

In some embodiments, the odor-control active comprises antimicrobial agents. For example, the odor-control active can include zinc pyrithione ("ZPT") and/or copper pyrithione ("CPT")). In some embodiments, the odor-control active comprises vapor phase antimicrobials. For example, the odor-control active can comprise essential oils (e.g., thymol, lemongrass, tea tree, etc.), chlorine dioxide and/or ethylene oxide.

Moreover, the odor-control active can include one or more of desiccant materials (e.g., a hygroscopic substance, such as calcium oxide or silica gel, that has a high affinity for water and is used as a drying agent), deodorizing agents (i.e., deodorizing compositions with a deodorizing effect on offensive odors such as that associated with activated nitrogen compound, activated sulfur compounds, etc.), and functional nanoparticles. In yet further embodiments, the odor-control active can include a trapping or an adsorbent/absorbent agent (e.g., zeolites, activated carbon, etc.).

As used herein, the term "odor" refers to any substance that can stimulate an olfactory response in a human; i.e., sense of smell. As used herein, the term "malodor" and any of its derivative terms refers to an odor that is generally considered unpleasant, obnoxious, or nauseating by the general population, such as the broad spectrum of odors associated with household trash, including odors related to stale urine, feces, vomitus, and putrefying organic materials, e.g., food waste, in common household trash. As used herein, the term "malodor particle" refers to a particle or molecule that carries a malodor. Though it will be understood that a malodor particle includes any particle or molecule that carries a malodor, examples of malodor particles include those derived from sulfide chemistries (e.g., dipropyl trisulfide, propyl mercaptan, dimethyl sulfide, dimethyl trisulfide, methal mercaptan, hydrogen sulfide, etc.), nitrogen chemistries (e.g., trimethylamine, trimethylamine, etc.), or aldehydes, keytones, and/or ester (e.g., demascenone, nonenal, pentanal, methinoal, pentyl acetate, etc.).

As used herein, the terms "lamination," "laminate," and "laminated film," refer to the process and resulting product made by bonding together two or more layers of film or other material. The term "bonding", when used in reference to bonding of multiple layers of a multi-layer film, may be used interchangeably with "lamination" of the layers. According to methods of the present disclosure, adjacent layers of a multi-layer film are laminated or bonded to one another. The bonding purposely results in a relatively weak bond between the layers that has a bond strength that is less than the strength of the weakest layer of the film. This allows the lamination bonds to fail before the film layer, and thus the bond, fails.

The term laminate is also inclusive of coextruded multi-layer films comprising one or more tie layers. As a verb, "laminate" means to affix or adhere (by means of, for example, adhesive bonding, pressure bonding, ultrasonic bonding, corona lamination, and the like) two or more separately made film articles to one another so as to form a multi-layer structure. As a noun, "laminate" means a product produced by the affixing or adhering just described.

As used herein the terms "partially discontinuous bonding" or "partially discontinuous lamination" refers to lamination of two or more layers where the lamination is substantially continuous in the machine direction or in the transverse direction, but not continuous in the other of the machine direction or the transverse direction. Alternately, partially discontinuous lamination refers to lamination of two or more layers where the lamination is substantially continuous in the width of the article but not continuous in the height of the article, or substantially continuous in the height of the article but not continuous in the width of the article. More particularly, partially discontinuous lamination refers to lamination of two or more layers with repeating bonded patterns broken up by repeating unbounded areas in either the machine direction or the transverse direction.

As used herein, the term "substantially," in reference to a given parameter, property, or condition, means to a degree that one of ordinary skill in the art would understand that the given parameter, property, or condition is met within a degree of variance, such as within acceptable manufacturing tolerances. By way of example, depending on the particular parameter, property, or condition that is substantially met, the parameter, property, or condition may be at least 90.0% met, at least 95.0% met, at least 99.0% met, or even at least 99.9% met.

As used herein, the term "flexible" refers to materials that are capable of being flexed or bent, especially repeatedly, such that they are pliant and yieldable in response to externally applied forces. Accordingly, "flexible" is substantially opposite in meaning to the terms inflexible, rigid, or unyielding. Materials and structures that are flexible, therefore, may be altered in shape and structure to accommodate external forces and to conform to the shape of objects brought into contact with them without losing their integrity. In accordance with further prior art materials, web materials are provided which exhibit an "elastic-like" behavior in the direction of applied strain without the use of added traditional elastic. As used herein, the term "elastic-like" describes the behavior of web materials which when subjected to an applied strain, the web materials extend in the direction of applied strain, and when the applied strain is released the web materials return, to a degree, to their pre-strained condition.

As used herein, any relational terms such as "first," "second," and "third," "inner," "outer," "upper," "lower," "side," "top," "bottom," etc. are for clarity and convenience in understanding the present disclosure and accompanying drawings and does not connote or depend on any specific preference, orientation, or order, except where the context clearly indicates otherwise. For example, the relational terms may refer an orientation of a multi-layer bag while disposed within a receptacle (e.g., a trash can) for use.

Film Materials

As an initial matter, the thermoplastic material of the films of one or more implementations of the present disclosure may include thermoplastic polyolefins, including polyethylene and copolymers thereof and polypropylene and copolymers thereof. The olefin-based polymers may include ethylene or propylene based polymers such as polyethylene, polypropylene, and copolymers such as ethylene vinyl acetate (EVA), ethylene methyl acrylate (EMA) and ethylene acrylic acid (EAA), or blends of such polyolefins.

Other examples of polymers suitable for use as films in accordance with the present disclosure may include elastomeric polymers. Suitable elastomeric polymers may also be biodegradable or environmentally degradable. Suitable elastomeric polymers for the film include poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), oriented poly(ethylene-terephthalate), poly(ethylene-butylacrylate), polyurethane, poly(ethylene-propylene-diene), ethylene-propylene rubber, nylon, etc.

Some of the examples and description herein below refer to films formed from linear low-density polyethylene. The term "linear low density polyethylene" (LLDPE) as used herein is defined to mean a copolymer of ethylene and a minor amount of an olefin containing 4 to 10 carbon atoms, having a density of from about 0.910 to about 0.926, and a melt index (MI) of from about 0.5 to about 10. For example, some examples herein use an octene comonomer, solution phase LLDPE (MI=1.1; ρ=0.920). Additionally, other examples use a gas phase LLDPE, which is a hexene gas phase LLDPE formulated with slip/AB (MI=1.0; ρ=0.920). Still further examples use a gas phase LLDPE, which is a hexene gas phase LLDPE formulated with slip/AB (MI=1.0; ρ=0.926). One will appreciate that the present disclosure is not limited to LLDPE, and can include "high density polyethylene" (HDPE), "low density polyethylene" (LDPE), and "very low density polyethylene" (VLDPE). Indeed, films made from any of the previously mentioned thermoplastic materials or combinations thereof can be suitable for use with the present disclosure.

Some embodiments of the present disclosure may include any flexible or pliable thermoplastic material that may be formed or drawn into a web or film. Furthermore, each thermoplastic film may include a single layer or multiple layers of thermoplastic materials as described in further detail below in regard to FIGS. 7A-7C. The thermoplastic material may be opaque, transparent, translucent, or tinted. Furthermore, the thermoplastic material may be gas permeable or impermeable.

Additional additives that may be included in one or more embodiments include slip agents, anti-block agents, voiding agents, or tackifiers. Additionally, one or more implementations of the present disclosure include films that are devoid of voiding agents. Some examples of inorganic voiding agents, which may further provide odor control, include the following but are not limited to: calcium carbonate, magnesium carbonate, barium carbonate, calcium sulfate, magnesium sulfate, barium sulfate, calcium oxide, magnesium oxide, titanium oxide, zinc oxide, aluminum hydroxide, magnesium hydroxide, talc, clay, silica, alumina, mica, glass powder, starch, charcoal, zeolites, any combination thereof, etc. Organic voiding agents, polymers that are immiscible in the major polymer matrix, can also be used. For instance, polystyrene can be used as a voiding agent in polyethylene and polypropylene films.

Further additives that may include in one or more embodiments include natural oils. For example, the additives may include thyme oil, mint oil, lemon grass oil, tea tree oil, cinnamon bark oil, methyl jasmonate, etc. Yet further additives may include zinc pyrithione ("ZPT") and copper pyrithione ("CPT"), which inhibit microbial growth.

One of ordinary skill in the art will appreciate in view of the present disclosure that manufacturers may form the films or webs to be used with the present disclosure using a wide variety of techniques. For example, a manufacturer can form a precursor mix of the thermoplastic material and one or more additives. The manufacturer can then form the film(s) from the precursor mix using conventional flat or cast extrusion or coextrusion to produce monolayer, bilayer, or multilayer films. Alternatively, a manufacturer can form the films using suitable processes, such as, a blown film process to produce monolayer, bilayer, or multilayer films. If desired for a given end use, the manufacturer can orient the films by trapped bubble, tenterframe, or other suitable process. Additionally, the manufacturer can optionally anneal the films thereafter.

An optional part of the film-making process is a procedure known as "orientation." The orientation of a polymer is a reference to its molecular organization, i.e., the orientation of molecules relative to each other. Similarly, the process of orientation is the process by which directionality (orientation) is imposed upon the polymeric arrangements in the film. The process of orientation is employed to impart desirable properties to films, including making cast films tougher (higher tensile properties). Depending on whether the film is made by casting as a flat film or by blowing as a tubular film, the orientation process can require different procedures. This is related to the different physical characteristics possessed by films made by the two conventional film-making processes; casting and blowing. Generally, blown films tend to have greater stiffness and toughness. By contrast, cast films usually have the advantages of greater film clarity and uniformity of thickness and flatness, generally permitting use of a wider range of polymers and producing a higher quality film.

When a film has been stretched in a single direction (monoaxial orientation), the resulting film can exhibit strength and stiffness along the direction of stretch, but can be weak in the other direction (i.e., across the stretch), often splitting when flexed or pulled. To overcome this limitation, two-way or biaxial orientation can be employed to more evenly distribute the strength qualities of the film in two directions. Most biaxial orientation processes use apparatus that stretches the film sequentially, first in one direction and then in the other.

In one or more implementations, the films of the present disclosure are blown film, or cast film. Blown film and cast film is formed by extrusion. The extruder used can be a conventional one using a die, which will provide the desired gauge. Some useful extruders are described in U.S. Pat. Nos. 4,814,135; 4,857,600; 5,076,988; 5,153,382; each of which are incorporated herein by reference in their entirety. Examples of various extruders, which can be used in producing the films to be used with the present disclosure, can be a single screw type modified with a blown film die, an air ring, and continuous take off equipment.

In one or more embodiments, a manufacturer can use multiple extruders to supply different melt streams, which a feed block can order into different channels of a multi-channel die. The multiple extruders can allow a manufacturer to form a multi-layer film with layers having different compositions. Such multi-layer film may later be non-continuously laminated with another layer of film.

In a blown film process, the die can be an upright cylinder with a circular opening. Rollers can pull molten plastic upward away from the die. An air-ring can cool the film as the film travels upwards. An air outlet can force compressed air into the center of the extruded circular profile, creating a bubble. The air can expand the extruded circular cross section by a multiple of the die diameter. This ratio is called the "blow-up ratio." When using a blown film process, the manufacturer can collapse the film to double the plies of the film. Alternatively, the manufacturer can cut and fold the film, or cut and leave the film unfolded.

In any event, in one or more embodiments, the extrusion process can orient the polymer chains of the blown film. In particular, the extrusion process can cause the polymer chains of the blown film to be predominantly oriented in the machine direction. The orientation of the polymer chains can result in an increased strength in the direction of the orientation. As used herein predominately oriented in a particular direction means that the polymer chains are more oriented in the particular direction than another direction. One will appreciate, however, that a film that is predominately oriented in a particular direction can still include polymer chains oriented in directions other than the particular direction. Thus, in one or more embodiments the initial or starting films (films before being stretched or bonded or laminated in accordance with the principles described herein) can comprise a blown film that is predominately oriented in the machine direction.

The process of blowing up the tubular stock or bubble can further orient the polymer chains of the blown film. In particular, the blow-up process can cause the polymer chains of the blown film to be bi-axially oriented. Despite being bi-axially oriented, in one or more embodiments the polymer chains of the blown film are predominantly oriented in the machine direction (i.e., oriented more in the machine direction than the transverse direction).

The films of one or more implementations of the present disclosure can have a starting gauge between about 0.1 mils to about 20 mils, suitably from about 0.2 mils to about 4 mils, suitably in the range of about 0.3 mils to about 2 mils, suitably from about 0.6 mils to about 1.25 mils, suitably from about 0.9 mils to about 1.1 mils, suitably from about 0.3 mils to about 0.7 mils, and suitably from about 0.4 mils and about 0.6 mils. Additionally, the starting gauge of films of one or more implementations of the present disclosure may not be uniform. Thus, the starting gauge of films of one or more implementations of the present disclosure may vary along the length and/or width of the film.

As an initial matter, one or more layers of the films described herein can comprise any flexible or pliable material comprising a thermoplastic material and that can be formed or drawn into a web or film. As described above, the film includes a plurality of layers of thermoplastic films. Each individual film layer may itself include a single layer or multiple layers. In other words, the individual layers of the multi-layer film may each themselves comprise a plurality of laminated layers. Such layers may be significantly more tightly bonded together than the bonding provided by the purposely weak discontinuous bonding in the finished multi-layer film. Both tight and relatively weak lamination can be accomplished by joining layers by mechanical pressure, joining layers with adhesives, joining with heat and pressure, spread coating, extrusion coating, and combinations thereof. Adjacent sub-layers of an individual layer may be coextruded. Coextrusion results in tight bonding so that the bond strength is greater than the tear resistance of the resulting laminate (i.e., rather than allowing adjacent layers to be peeled apart through breakage of the lamination bonds, the film will tear).

The following discussion provides more detail with regards to one or more embodiments with reference to the figures. One or more embodiments of the present disclosure include products made from or with thermoplastic films and that include encapsulated odor control components. For example, such products include, but are not limited to, grocery bags, trash bags, sacks, and packaging materials, feminine hygiene products, baby diapers, adult incontinence products, or other products. For ease in description, however, the figures and bulk of the following disclosure focuses on films and bags. One will further appreciate that the teachings and disclosure equally applies to other products as well. For example, some embodiments of the present disclosure include nonwovens in place of the films described herein. Additional embodiments of the present disclosure include other materials in place of the films described herein.

Referring now to the figures, FIG. 1 is a perspective view of a thermoplastic bag 100 according to an embodiment of the present disclosure. The thermoplastic bag 100 includes a first sidewall 102 and a second sidewall 104. Each of the first and second sidewalls 102, 104 includes a first side edge 106, a second opposite side edge 108, a bottom edge 110 extending between the first and second side edges 106, 108, and top edge 111 extending between the first and second side edges 106, 108 opposite the bottom edge 110. In some embodiments, the first sidewall 102 and the second sidewall 104 are joined together along the first side edges 106, the second opposite side edges 108, and the bottom edges 110. The first and second sidewalls 102, 104 may be joined along the first and second side edges 106, 108 and bottom edges 110 by any suitable process such as, for example, a heat seal.

In some embodiments, the bottom edge 110 or one or more of the side edges 106, 108 can comprise a fold. In other words, the first and second sidewalls 102, 104 may comprise a single unitary piece of material. The top edges 111 of the first and second sidewalls 102, 104 may define an opening 112 to an interior of the thermoplastic bag 100. In other words, the opening 112 may be oriented opposite the bottom edge 110 of the thermoplastic bag 100. Furthermore, when placed in a trash receptacle, the top edges 111 of the first and second sidewalls 102, 104 may be folded over the rim of the receptacle.

In some embodiments, the thermoplastic bag 100 may optionally include a closure mechanism 114 located adjacent to the top edges 111 for sealing the top of the thermoplastic bag 100 to form an at least substantially fully-enclosed container or vessel. As shown in FIG. 1, in some embodiments, the closure mechanism 114 comprises a draw tape 116, a first hem 120, and a second hem 118. In particular, the first top edge 111 of the first sidewall 102 may be folded back into the interior volume and may be attached to an interior surface of the first sidewall 102 to form the first hem 120. Similarly, the second top edge 111 of the second sidewall 104 is folded back into the interior volume and may be attached to an interior surface of the second sidewall 104 to form a second hem 118. The draw tape 116 extends through the first and second hems 120, 118 along the first and second top edges 111. The first hem 120 includes a first aperture 124 (e.g., notch) extending through the first hem 120 and exposing a portion of the draw tape 116. Similarly, the second hem 118 includes a second aperture 122 extending through the second hem 118 and exposing another portion of the draw tape 116. During use, pulling the draw tape 116 through the first and second apertures 124, 122 will cause the first and second top edges 111 to constrict. As a result, pulling the draw tape 116 through the first and second apertures 124, 122 will cause the opening 112 of the multi-layer bag to at least partially close or reduce in size. The draw tape closure mechanism 114 may be used with any of the implementations of a reinforced thermoplastic bag described herein.

Although the thermoplastic bag 100 is described herein as including a draw tape closure mechanism 114, one of ordinary skill in the art will readily recognize that other closure mechanisms may be implemented into the thermoplastic bag 100. For example, in some embodiments, the closure mechanism 114 may include one or more of flaps or handles, adhesive tapes, a tuck and fold closure, an interlocking closure, a slider closure, a zipper closure, or any other closure structures known to those skilled in the art for closing a bag.

Figure 2:
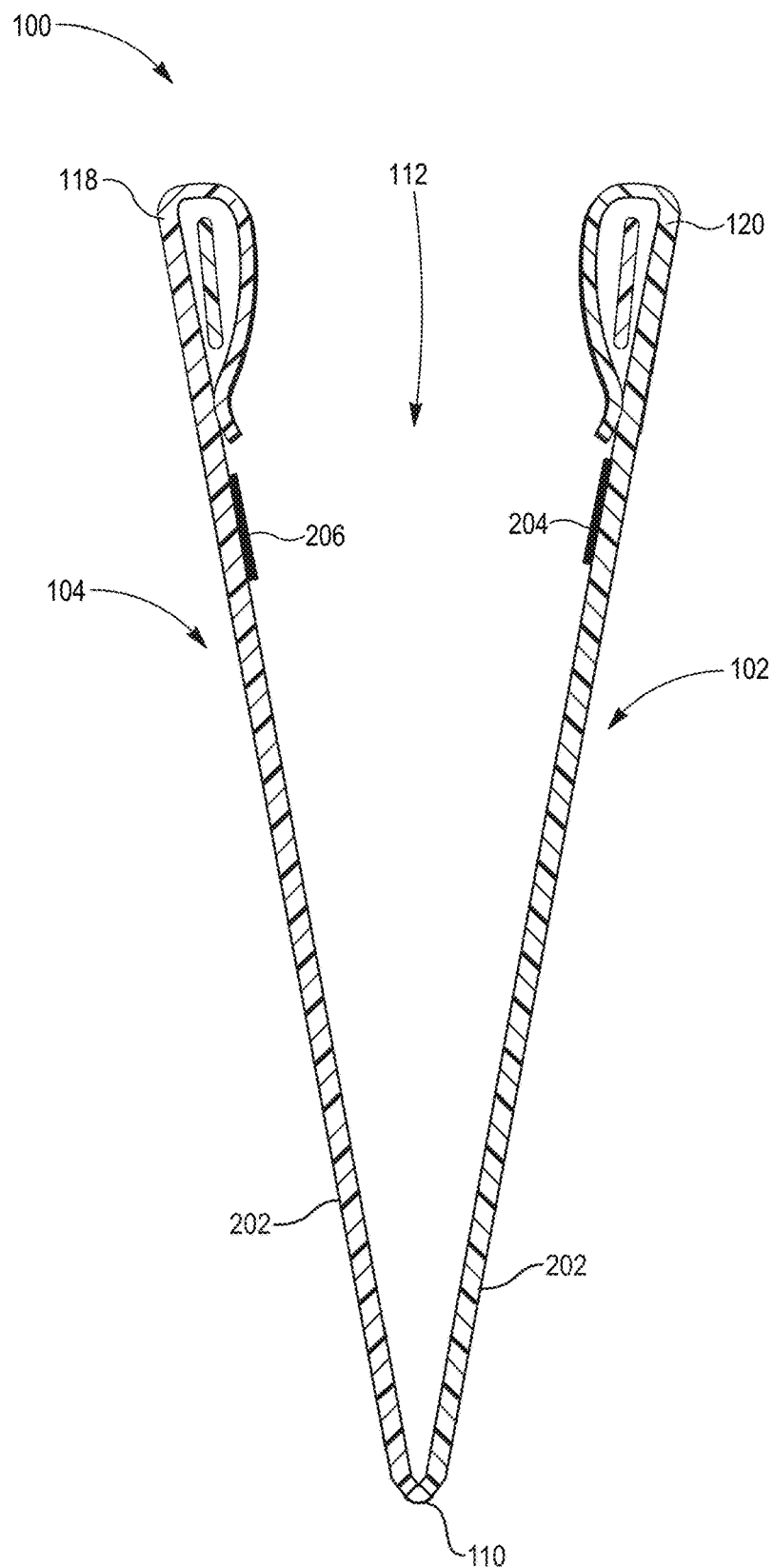
FIG. 2 illustrates a side cross-sectional view of a thermoplastic bag having an encapsulated odor control component in accordance with one or more embodiments.

FIG. 2 illustrates a side cross-sectional view of the thermoplastic bag 100 of FIG. 1 having the encapsulated odor control component disposed thereon in accordance with one or more embodiments. As shown in FIG. 2, each of the first sidewall 102 and the second sidewall 104 of the thermoplastic bag 100 includes a single layer of thermoplastic film 202. The thermoplastic film 202 of the first sidewall 102 and the second sidewall 104 can include any of the thermoplastic films described above. In one or more embodiments, each of the first and second sidewalls 102, 104 of the thermoplastic bag 100 includes multiple layers of thermoplastic film as will be discussed in more detail with reference to FIGS. 6A-6B. Additionally, as shown in FIG. 2, the thermoplastic bag 100 includes the encapsulated odor control component disposed as a first strip 204 and a second strip 206 onto the first sidewall 102 and the second sidewall 104, respectively. Though not shown, some embodiments involve coextruding the encapsulated odor control component with the first sidewall 102 and the second sidewall 104 (i.e., embedding the encapsulated odor control component as an additive into the thermoplastic film forming the first sidewall 102 and the second sidewall 104 during the extrusion process) as discussed above.

As mentioned briefly above, the encapsulated odor control component can be disposed as a first strip 204 and a second strip 206 onto the first sidewall 102 and the second sidewall 104, respectively. As shown in FIG. 2, the first strip 204 and the second strip 206 can be disposed on an interior surface of the respective sidewall (i.e., the surface of the sidewall facing the opening 112 of the thermoplastic bag 100). In some embodiments, however, the first strip 204 and the second strip 206 are disposed on an exterior surface of the respective sidewall. Additionally, though FIG. 2 illustrates the first strip 204 and the second strip 206 positioned near the top of the respective sidewall, in one or more embodiments, the strips can be positioned lower.

In some embodiments, the encapsulated odor control component of the first strip 204 and the encapsulated odor control component of the second strip 206 include different odor-control actives. For example, the encapsulated odor control component of the first strip 204 can include a first odor-control active that includes a deodorizing agent and the encapsulated odor control component of the second strip 206 can include a second odor-control active that includes a volatile fragrance material. In another non-limiting example, the encapsulated odor control component of the first strip 204 includes a first odor-control active that includes a deodorizing agent, the encapsulated odor control component of the second strip 206 includes a second odor-control active that includes an antimicrobial agent, and the encapsulated odor control component of a third strip (not shown) includes a third odor-control active that includes a volatile fragrance material. Furthermore, in some embodiments, an odor-control active including a volatile fragrance material can include a plurality of different components to render scents of different expressions (e.g., intensity and/character).

In one or more embodiments, the encapsulated odor control component of each strip is configured to release an odor-control active when exposed to different sets of malodor particles. For example, the first strip 204 can be configured to release the first odor-control active when exposed to a first set of malodor particles and the encapsulated odor control component of the second strip 206 can be configured to release the second odor-control active when exposed to a second set of malodor particles. More specifically, in one or more embodiments, each encapsulated odor control component is configured to release an odor-control active when exposed to malodor particles having a chemical structure that provides the malodor particles with a particular pH level. For example, the first strip 204 can be configured to release the first odor-control active when exposed to malodor particles having a first chemical structure giving the malodor particles a first pH value (or pH values within a first range of pH values) and the second strip 206 can be configured to release the second odor-control active when exposed to malodor particles having a second chemical structure giving the malodor particles a second pH value (or pH values within a second range of pH values). In this way, the thermoplastic bag 100 can provide odor control over a broad array of malodors.

While FIG. 2 illustrates the encapsulated odor control component in the form of a strip, in other embodiments, the encapsulated odor control component can be applied to the thermoplastic bag 100 in other forms. For example, the encapsulated odor control component can be applied as a dot, streak, or in a full surface application.

In still further embodiments, a bag can comprise both non-encapsulated odor control actives and encapsulated odor control actives. The non-encapsulated odor control actives can be the same as, or differ, from the encapsulated odor control actives. For example, a thermoplastic bag can comprise a first encapsulated odor control active and a second non-encapsulated odor control active. In one or more embodiments, the non-encapsulated odor control active is a fragrance (e.g., neat fragrance oil) that provides the bag with a pleasant smell irrespective of the presence of malodor. In contrast, the encapsulated odor control active can respond to the presence of malodor particles as described above. In such embodiments, the encapsulated odor control active can be released after some or all of the fragrance has been exhausted so as to provide the bag with varying/longer malodor protection.

Figure 3A:
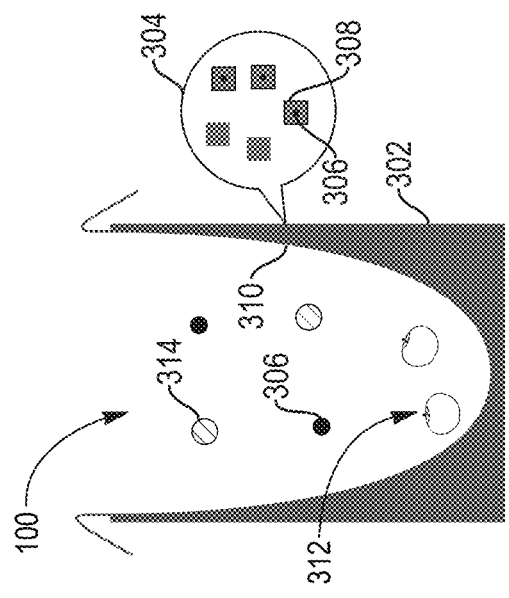
FIGS. 3A-3C illustrate a sequence wherein an odor control component releases an odor-control active in the presence of malodor particles in accordance with one or more embodiments.
Figure 3B:
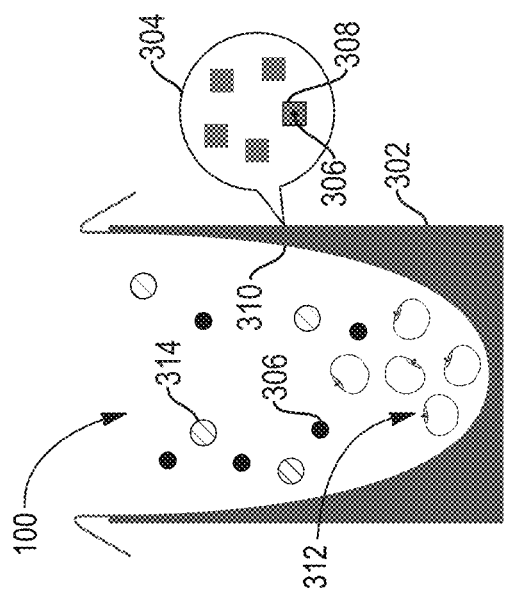
Figure 3C:
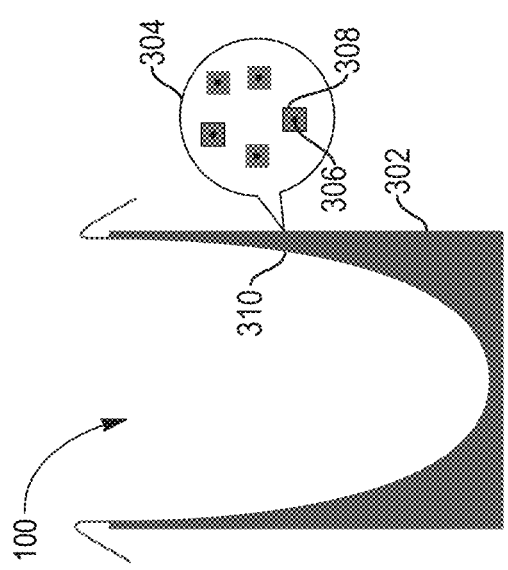

As mentioned above, the thermoplastic bag 100 can include an encapsulated odor control component configured to release an odor-control active when exposed to malodor particles. FIGS. 3A-3C illustrate operation of the encapsulated odor control component in the presence of malodor particles in accordance with one or more embodiments. In particular, FIG. 3A illustrates the thermoplastic bag 100 including encapsulated odor control components and positioned within a trash receptacle 302. The thermoplastic bag 100 includes a plurality of encapsulated odor control components 304 disposed on a segment 310 of the thermoplastic bag 100. In particular, each encapsulated odor control component of the plurality of encapsulated odor control components 304 includes an odor-control active 306 encapsulated within an odor-control encapsulant 308.

As shown in FIG. 3A, there are no malodor sources (e.g., articles of trash) within the thermoplastic bag 100; therefore, no malodor particles are present. Accordingly, the encapsulated odor control components within the set of encapsulated odor control components 304 do not release their respective odor-control active 306. This is ideal to prevent exhausting the odor-control active supply when there is no malodor to control.

FIG. 3B shows another embodiment of the thermoplastic bag 100 including encapsulated odor control components and positioned within the trash receptacle 302. In particular, FIG. 3B illustrates the thermoplastic bag 100 after a set of malodor sources 312 have been added. As shown, the set of malodor sources 312 produce malodor particles 314.

In response to the presence of the malodor particles 314 several encapsulated odor control components from the plurality of encapsulated odor control components 304 release their respective odor-control active 306 while others maintain their respective odor-control active 306 encapsulated. In some embodiments, every encapsulated odor control component from the plurality of encapsulated odor control components 304 releases its respective odor-control active 306 in the presence of the malodor particles 314. However, the embodiments in which only some of the encapsulated odor control components release their respective odor-control active 306 provides an advantageous controlled release that avoids exhausting the entire odor-control active supply in the presence of a low quantity of malodor particles.

FIG. 3C illustrates another embodiment of the thermoplastic bag 100 including encapsulated odor control components and positioned within the trash receptacle 302. In particular, FIG. 3C illustrates the thermoplastic bag 100 after additional malodor sources have been added to the set of malodor sources 312. As shown, because the set of malodor sources 312 now includes additional malodor sources, the set of malodor sources 312 produces additional malodor particles 314. In response to the presence of the additional malodor particles 314, additional encapsulated odor control components from the plurality of encapsulated odor control components 304 release their respective odor-control active 306. This ideally enables the thermoplastic bag 100 to control malodors produced by trash that is added over a period of time.

It should be noted that the set of malodor sources 312 portrayed in FIGS. 3B-3C do not contact the segment 310 of the thermoplastic bag 100 on which the plurality of encapsulated odor control components 304 is disposed. In particular, the encapsulated odor control components do not require direct contact with the malodor sources in order to release their respective odor-control active 306. Rather, encapsulated odor control components are configured to release the odor-control active 306 from the odor-control encapsulant 308 when exposed to malodors (i.e., malodor particles).

The release of the odor-control active 306 in the presence of malodor advantageously enables the plurality of encapsulated odor control components 304 to contribute to odor control at all stages of use of the thermoplastic bag 100. Additionally, this enables the plurality of encapsulated odor control components 304 to contribute to the control of malodors produced by malodor sources not in contact with any surface of the thermoplastic bag 100 (e.g., centered within the thermoplastic bag 100, surrounded by other trash, etc.).

Figure 4:
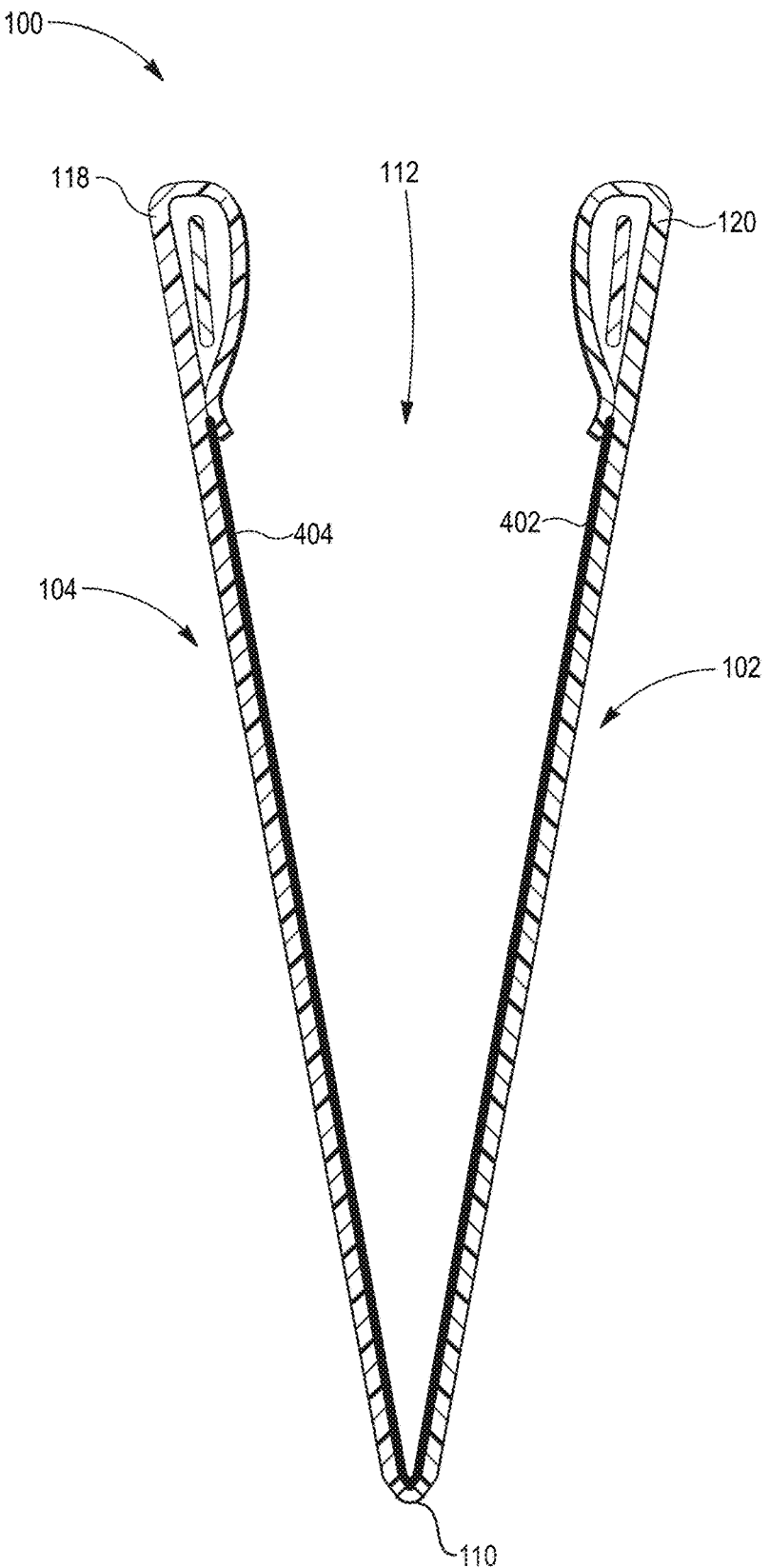
FIG. 4 illustrates a side cross-sectional view of another thermoplastic bag having an encapsulated odor control component in accordance with one or more embodiments.

Configuring the encapsulated odor control component to release the odor-control active based on exposure to malodor particles (rather than requiring direct contact with the malodor sources themselves) enables disposition of the encapsulated odor control component onto the thermoplastic bag 100 in a variety of ways (i.e., other than the strips illustrated in FIG. 2). FIG. 4 illustrates another side cross-sectional view of the thermoplastic bag 100 of FIG. 1 having the encapsulated odor control component disposed thereon in accordance with one or more embodiments. As shown in FIG. 4, the thermoplastic bag 100 includes the encapsulated odor control component 402 disposed to cover an interior surface of the first sidewall 102 (i.e., the surface of the sidewall facing the opening 112 of the thermoplastic bag 100) and the encapsulated odor control component 404 disposed to cover the interior surface of the second sidewall 104. In one or more embodiments, the encapsulated odor control components 402, 404 include the same odor-control active. In some embodiments, the encapsulated odor control components 402, 404 include different odor-control actives as discussed with reference to FIG. 2. In further embodiments, the encapsulated odor control components 402, 404 are configured to release their respective odor-control active when exposed to different sets of malodor particles. By disposing the encapsulated odor control component to cover the entire surface of the sidewalls, the thermoplastic bag 100 can supply a greater amount of odor-control active to control greater amounts of malodors.

In one or more embodiments, the amount of surface area covered by the encapsulated odor control component impacts the rate of release of odor-control active. For example, covering a larger surface area of a thermoplastic bag with the encapsulated odor control component (e.g., covering the entire interior surface of the sidewalls 102, 104 of the thermoplastic bag 100, as shown in FIG. 4) can increase the rate of release of odor-control active as a larger amount of encapsulated odor control component is exposed to (i.e., triggered to release odor-control active by) malodor particles. Further, covering a smaller surface area of a thermoplastic bag with the encapsulated odor control component (e.g., disposing strips of the encapsulated odor control component onto the sidewalls 102, 104 of the thermoplastic bag 100, as shown in FIG. 2) can decrease the rate of release of odor control active as smaller amount of encapsulated odor control component is exposed to malodor particles. Therefore, in one or more embodiments, the rate of release of odor-control active can be controlled by controlling the amount of surface area covered by the encapsulated odor control component.

Figure 5:
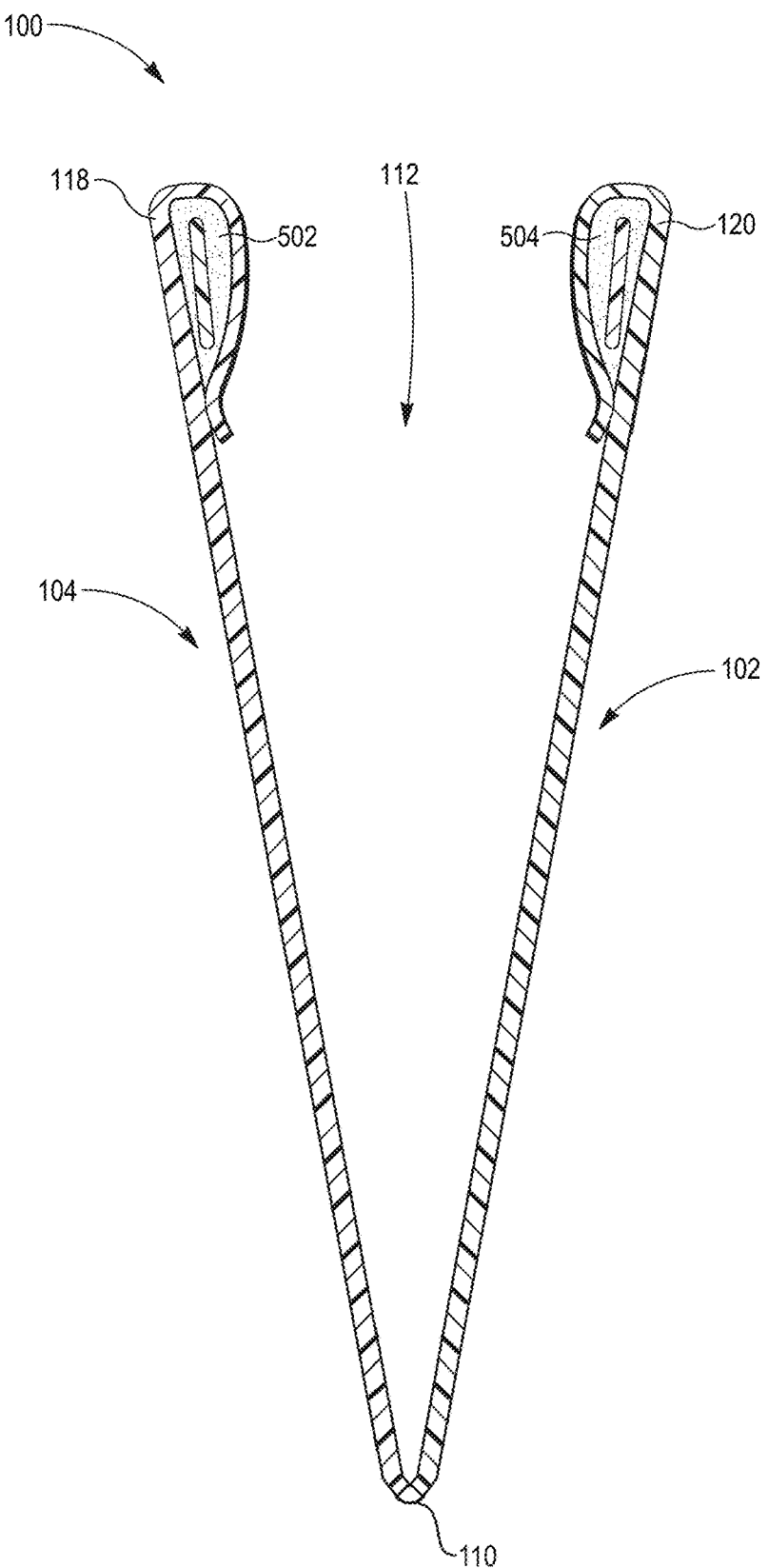
FIG. 5 illustrates a side cross-sectional view of yet another thermoplastic bag having an encapsulated odor control component in accordance with one or more embodiments.

FIG. 5 illustrates another side cross-sectional view of the thermoplastic bag 100 of FIG. 1 having the encapsulated odor control component disposed thereon in accordance with one or more embodiments. As shown in FIG. 5, the thermoplastic bag 100 includes the encapsulated odor control component 504 disposed with a first hem 120 and the encapsulated odor control component 502 disposed with a second hem 118 of the thermoplastic bag 100. In one or more embodiments, the encapsulated odor control components 502, 504 include the same odor-control active. In some embodiments, the encapsulated odor control components 502, 504 include different odor-control actives as discussed with reference to FIG. 2. In further embodiments, the encapsulated odor control components 502, 504 are configured to release their respective odor-control active when exposed to different sets of malodor particles. By disposing the encapsulated odor control component within the hems, the thermoplastic bag 100 can include encapsulated odor control components applications that are not consumer friendly (e.g., not visually attractive, sticky, oily, powder, etc.) as will be discussed in more detail with regards to FIGS. 6A-6B.

Figure 6A:
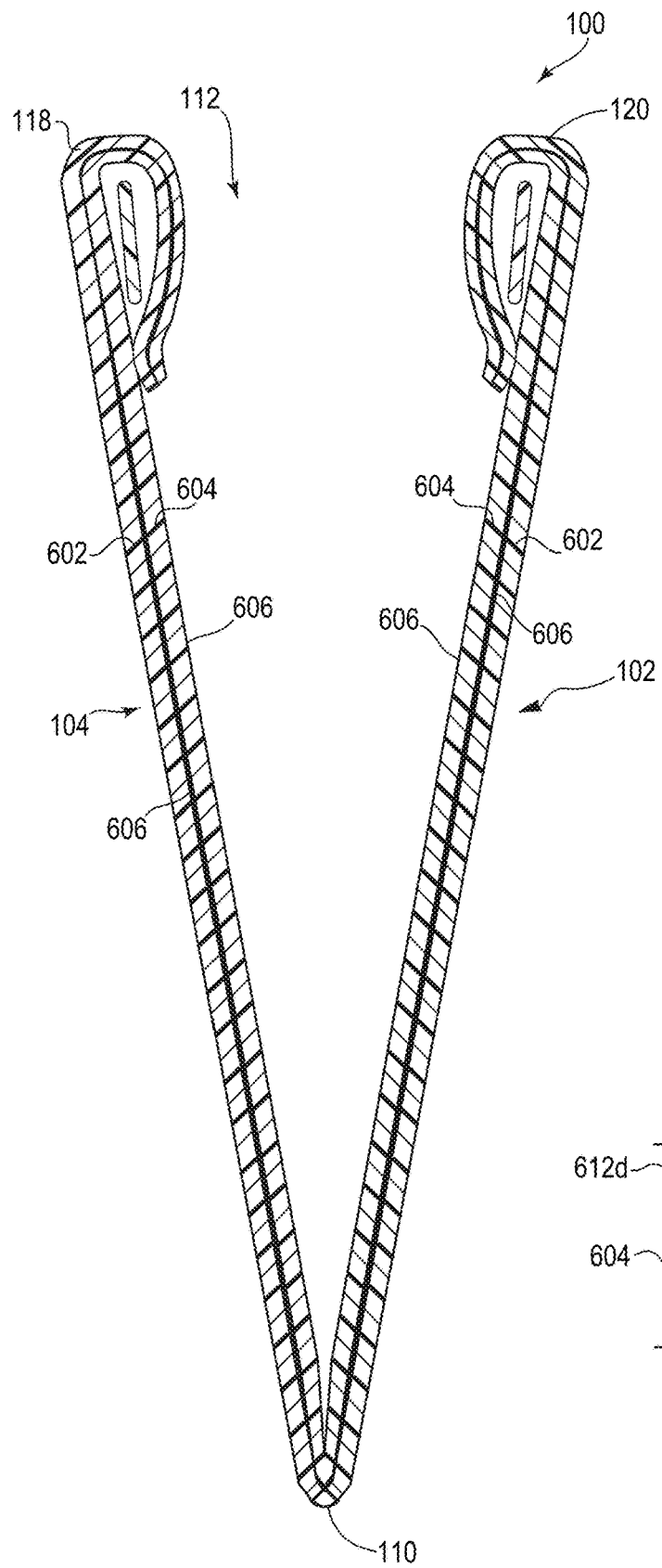
FIG. 6A illustrates a side cross-sectional view of yet another thermoplastic bag having an encapsulated odor control component in accordance with one or more embodiments.
Figure 6B:
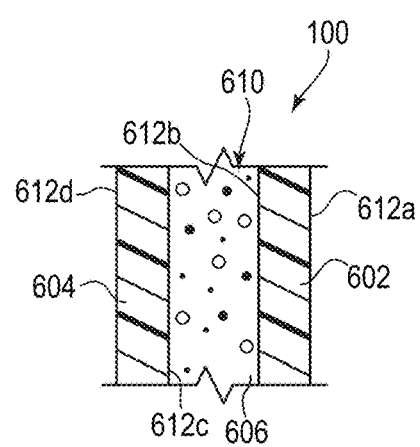
FIG. 6B shows an enlarged partial side cross-sectional view of a sidewall of the thermoplastic bag of FIG. 6A.

FIG. 6A is a side cross-sectional view of the thermoplastic bag 100 of FIG. 1. FIG. 6B is an enlarged view of the side cross-sectional view of the thermoplastic bag 100 of FIG. 6A. Referring to FIGS. 6A and 6B together, each of the first and second sidewalls 102, 104 of the thermoplastic bag 100 includes multiple layers of thermoplastic film. In particular, each of the first and second sidewalls 102, 104 includes a first film 602 and a second film 604. The thermoplastic bag 100 further comprises an odor control component 606 disposed on one or more of the first and second films 602, 604. When disposed within a receptacle (e.g., trash can), the first film 602 of each of the first and second sidewalls 102, 104 (referred to herein collectively as "the first film 602") of the thermoplastic bag 100 may face (e.g., be oriented adjacent and proximate to) the receptacle, and the second film 604 of each of the first and second sidewalls 102, 104 (referred to herein collectively as "the second film 604") may face (e.g., at least partially define) the interior of the of the thermoplastic bag 100.

The first and second films 602, 604 may include films such as any of the films described above. As mentioned briefly above, the encapsulated odor control component 606 may be disposed on one or more of the first film 602 and the second film 604. Specifically, the first and second films 602, 604 may be at least partially dosed with the encapsulated odor control component 606. The encapsulated odor control component can 606 be disposed between the first and second films 602, 604. As used herein, the term "between," when referring to the odor control component 606 and the first and second films 602, 602, means that the encapsulated odor control component 606 is disposed at least partially within a space separating at least a portion of the first film 602 and at least a portion of the second film 604. Thus, the encapsulated odor control component 606 can be disposed on one or more of the first and second films 602, 604 (e.g., on a side of the first and second films 602, 604 facing the space separating the films 602, 604 from each other). Furthermore, the encapsulated odor control component 606 can be disposed at least partially in (e.g., at least partially embedded in) one or more of the first and second films 602, 604.

In some embodiments, the encapsulated odor control component 606 can at least substantially fully span an area between the first film 602 and the second film 604. In other words, the odor control component 606 can at least substantially fully span a length and width of the first and second films 602, 604. In other embodiments, the encapsulated odor control component 606 may be disposed between only portions of the first and second films 602, 604. In other words, the encapsulated odor control component 606 may not be continuous and may span only portions of the area between the first film 602 and the second film 604. In additional embodiments, the encapsulated odor control component 606 is included in the first and second films 602, 604 (via inclusion in master batch used to form the first and second films 602, 604) in addition to being disposed between the first and second films 602, 604.

In some embodiments, the first and second sidewalls 102, 104 include an air gap 610 between the first and second films 602, 604 that works in conjunction with the encapsulated odor control component 606. In particular, the air gap 610 provides a means of trapping malodor. For example, malodor can pass into the air gap 610 and be at least partially trapped within the air gap 610. Thus, the air gap 610 can reduce or prevent malodor from passing through the outer film 602 of the thermoplastic bag 100. Additionally, one or more embodiments include an encapsulated odor control component within the air gap 610 that can help absorb or trap malodor. Additionally, encapsulated odor control components within the air gap 610 can influence the transmission rate or allow for a delay release. Furthermore, one or more embodiments involve using the air gap 610 to alter the pH of odoriferous species and mitigate formation of odor causing agents.

The air gap 610 can provide an area for disposition of the encapsulated odor control component 606 that conceals the encapsulated odor control component 606. Thus, one or more embodiments includes an encapsulated odor control component unsuitable for use in an unconcealed portion of a bag. For example, the encapsulated odor control component 606 between the first and second films 602, 604 can comprise an encapsulated odor control component 606 that lacks aesthetically pleasing characteristics generally desired by consumers. In another embodiment, the encapsulated odor control component 606 comprises negative effects to a consumer, such as skin irritation issues, dust inhalation issues, or other negative effects when combined with consumer interaction. In another embodiment, the encapsulated odor control component 606 is disposed in a wet (i.e., liquid) application that can have a negative effect for users of the bag. The air gap 610 can prevent a user from touching or accessing such wet odor control components.

In one or more embodiments, the encapsulated odor control component 606 produces malodor reduction without an added fragrance. Such an encapsulated odor control component 606 can be used to provide an unscented odor control bag or used in combination with a fragrance.

In additional embodiments, the encapsulated odor control component 606 comprises natural oils. For example, the encapsulated odor control component 606 may include thyme oil, mint oil, lemon grass oil, tea tree oil, cinnamon bark oil, methyl jasmonate, etc.

Additionally, the ability to place more volatile perfume materials in between layers is helpful in preserving longevity and synergy. In particular, the capability to place a portion of perfume between films can avoid initial fragrance intensity issues (e.g., releasing too much of a fragrance material and causing a resulting smell to be too strong). Along similar lines, the ability to place an encapsulated odor control component in the air gap between the first and second films 602, 604 can facilitate higher levels of perfume dosing without exposing a user to an oily feel inside the bag. Thus, the encapsulated odor control component 606 can comprise perfume technologies, higher levels of perfume, diethanol amine, triethanol amine, sulfur scavengers, molecular sieves, etc.

Furthermore, in some embodiments, the location where the encapsulated odor control component 606 is disposed between the first film 602 and the second film 604 may be selected based on where the malodor particles will be located relative to the thermoplastic bag 100. For example, the encapsulated odor control component 606 may be disposed between the first film 602 and the second film 604 at the bottom area of the thermoplastic bag 100 (e.g., a portion of the bag most likely to be exposed to malodor molecules). Furthermore, in some embodiments, the one or more substances of the encapsulated odor control component 606 may be selected based on where the encapsulated odor control component 606 will be located relative to the thermoplastic bag 100. For example, deodorizing agents may be selected for portions of the encapsulated odor control component 606 located at the bottom portion of the thermoplastic bag 100, and fragrance materials may be selected for portions of the encapsulated odor control component 606 located at the top portion of the thermoplastic bag 100.

In some embodiments, the encapsulated odor control component 606 may include a plurality of different odor-control actives. For example, the encapsulated odor control component 606 may include a first odor-control active including a deodorizing agent and a second odor-control active including a volatile fragrance material. In another non-limiting example, the encapsulated odor control component 606 may include a first odor-control active including a deodorizing agent, a second odor-control active including an antimicrobial agent, and a third odor-control active including a volatile fragrance material. Furthermore, in some embodiments, the encapsulated odor control component 606 may include a plurality of different components to render scents of different expressions (e.g., intensity and/character).

As shown in FIGS. 6A and 6B, the inner surface 612d of the thermoplastic bag 100 can have a first surface area. Typically, the inner surface 612d is the only surface upon which odor control components are applied. One will appreciate in light of the disclosure herein that the thermoplastic bag 100 includes additional surfaces 612b and 612c (i.e., the surfaces of the inner and outer films 602, 604 facing each other and forming the air gap 610). Thus, in one or more embodiments, the thermoplastic bag 100 can have odor control components 606 applied to a total surface area that is greater than the surface area of the inside layer of the thermoplastic bag 100 (i.e., by applying odor control components to surfaces 612a, 612b, and/or 612c).

The encapsulated odor control component 606 may help to reduce an amount of malodor molecules (e.g., bad smelling molecules) that permeate through the multiple layers of thermoplastic film of the first and second sidewalls 102, 104 of the thermoplastic bag 100.

Referring still to FIGS. 6A and 6B, disposing the encapsulated odor control component 606 between the first film 602 and the second film 604 instead of disposing the encapsulated odor control component 606 on a single side of a single layer film may enhance a release of the odor-control active of the encapsulated odor control component 606. Specifically, disposing the encapsulated odor control component 606 between the first film 602 and the second film 604 may provide control of a rate at which the odor-control active of the encapsulated odor control component 606 is released and/or a direction in which the odor-control active of the encapsulated odor control component 606 is released.

In one or more embodiments, the encapsulated odor control component 606 may comprise a bonding layer. In other words, the encapsulated odor control component 606 may at least partially bond the first film 602 to the second film 604. For example, the encapsulated odor control component 606 may include one or more of an adhesive, glue, tackifier, tapes, or any other known material for bonding films together. In such embodiments, the encapsulated odor control component 606 may also include the one or more substances described above (e.g., volatile fragrance materials and deodorizing agents).

Figure 7C:
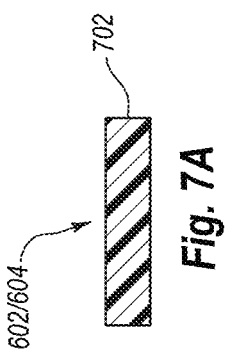
FIGS. 7A-7C show partial side cross-sectional views of films having varying numbers of layers.
Figure 7B:
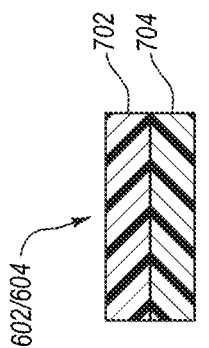
Figure 7A:
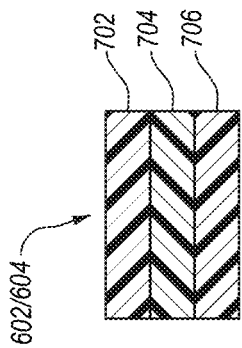

FIGS. 7A-7C are partial cross-sectional views of films that may be used herein as the first and second films 602, 604 of FIGS. 6A-6B. Referring to FIGS. 6A-7C together, in some embodiments, one or more of the first and second films 602, 604 may include a single first layer 702, as shown in FIG. 7A. In other embodiments, one or more of the first and second films 602, 604 may include two layers (i.e., a bi-layer film), as shown in FIG. 7B. For example, the first film 602 may include a first layer 702 and a second layer 704. In such embodiments, the first and second layers 702, 704 may optionally include different grades of thermoplastic material and/or include different additives, including polymer additives. In yet other embodiments, one or more of the first and second films 602, 604 may include three layers 702, 704, 706 (i.e., a tri-layer film), as shown in FIG. 7C. For example, the first film 602 may include a first layer 702, a second layer 704, and a third layer 706. In yet other embodiments, one of more of the first and second films 602, 604 may include more than three layers. In one or more embodiments, the layers of the first and second films 602, 604 are coextruded.

Figure 8B:
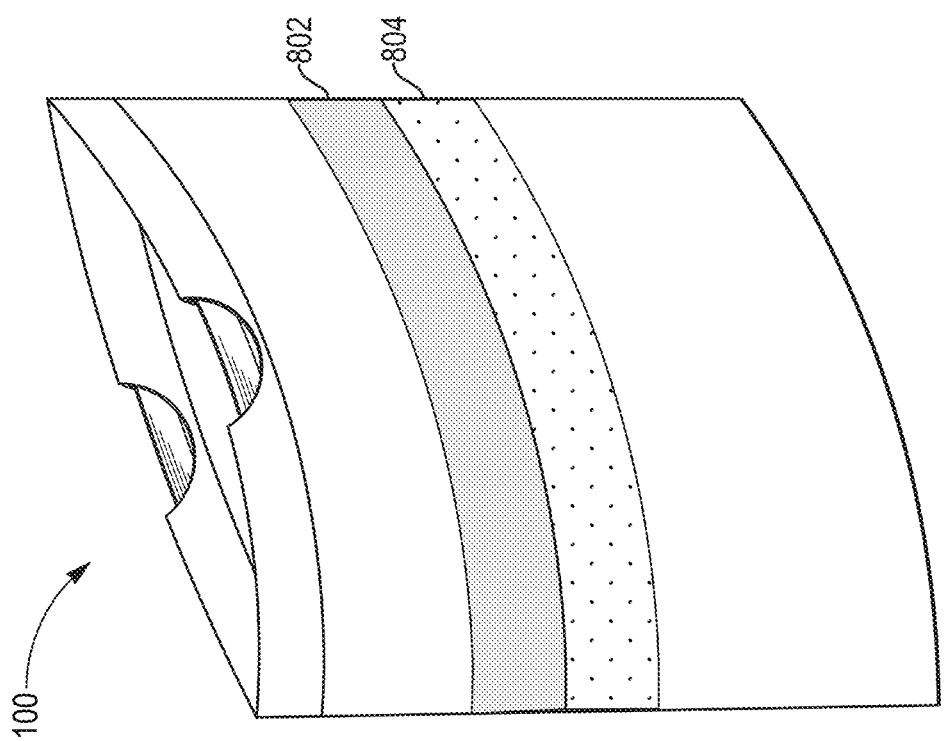
FIGS. 8A-8B illustrate a perspective view of a thermoplastic bag having a color indicator in accordance with one or more embodiments.
Figure 8A:
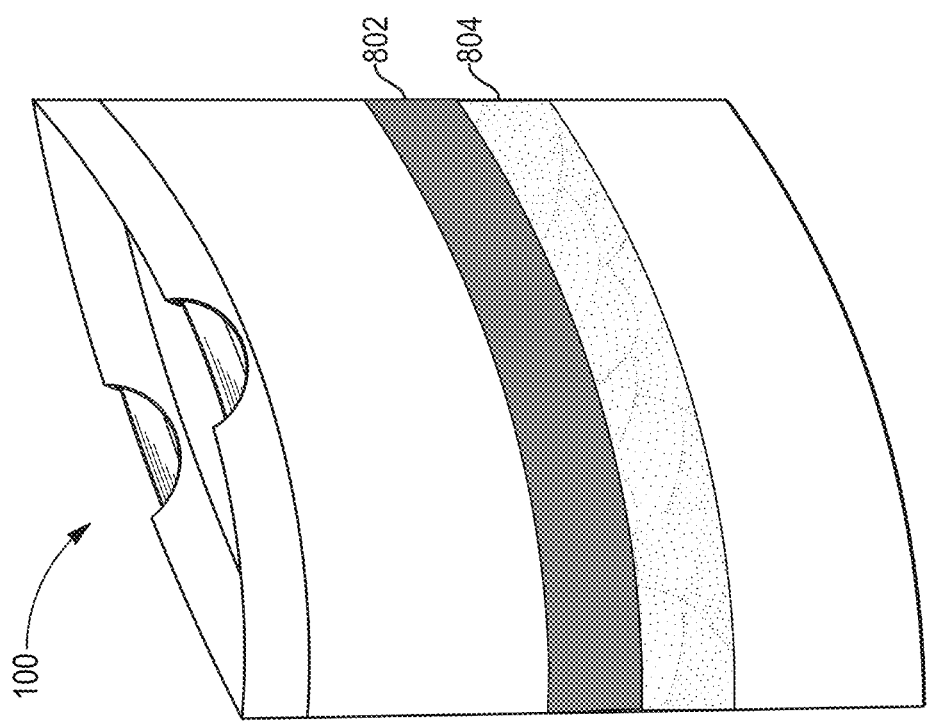

As mentioned above, in one or more embodiments, the thermoplastic bag 100 further includes a color indicator to indicate performance of the encapsulated odor control component. In particular, the color indicator is configured to change from a first color to a second color to indicate when the encapsulated odor control component has released the odor-control active. FIGS. 8A-8B illustrate the thermoplastic bag 100 including a color indicator in accordance with one or more embodiments. In particular, FIG. 8A illustrates the thermoplastic bag 100 including the color indicator 802 and the encapsulated odor control component 804. Specifically, FIG. 8A illustrates the color indicator 802 having a first color and a large quantity of the encapsulated odor control component 804. Although FIG. 8A illustrates the color indicator 802 positioned adjacent to the encapsulated odor control component 804, it will be appreciated that the color indicator 802 and the encapsulated odor control component 804 can be positioned anywhere on the thermoplastic bag 100—including in the same location (e.g., layered on top of one another)—without losing efficacy.

As the odor control component 804 is exposed to malodor particles (e.g., a consumer discards one or more malodor sources into the thermoplastic bag), the odor control component 804 releases the odor-control active. Simultaneously, the color indicator 802 changes from a first color to a second color to indicate the release.

In one or more embodiments, the color indicator 802 changes color based on exposure to the malodor particles. In particular, the color indicator 802 can be configured to change colors based on a pH level of the malodor particles. For example, in some embodiments, the color indicator 802 is configured to change colors when exposed to malodor particles having a pH level of 10. Some examples of such pH-driven color indicators include methyl violet, thymol blue, methyl orange, bromocresol green, methyl red, litmus, bromothymol blue, phenol red, phenolphthalein, thymolphthalein, alizarin yellow R, and anthocyanin.

In some embodiments, the color indicator 802 changes color based on exposure to moisture. In particular, as malodor sources are added to the thermoplastic bag 100, any moisture provided by the malodor sources (e.g., moisture vapor resulting from evaporation) can trigger the color indicator 802 to change colors. As a non-limiting example, a moisture-driven color indicator can include general transition metal complexes (e.g., cobalt chloride).

In further embodiments, the color indicator 802 changes color as a result of oxidation. As an example, magnesium dioxide (a yellow/brown color) can produce a manganite ion (a green color) through oxidation, which can produce a permanganate ion (a purple color) through further oxidation. As another example, methylene blue turns a blue color when oxidized but becomes clear when reduced.

In one or more embodiments, the color indicator 802 slowly fades in color as the encapsulated odor control component 804 releases odor-control active. For example, in some embodiments, the color indicator 802 includes a chromophore having chemical bonds that oxidize as the odor-control active is released. The oxidation can shift the absorption of the chromophore outside the visible light spectrum. Alternatively, the oxidation can remove the chromophore's ability to absorb light and emit a color altogether.

In some embodiments, the color indicator 802 changes color based on exposure to the odor-control active itself. For example, the odor-control active can have a pH level that causes the color indicator 802 to change color. Accordingly, when the encapsulated odor control component 804 releases the odor-control active, exposure to the odor-control active can cause the color indicator 802 to change colors. Consequently, the color indicator 802 can change colors more quickly when exposed to both malodor particles and the odor-control active having a pH value that would induce a color change. In other words, the rate of change from the first color to the second color can be based, at least in part, on the pH level of the odor-control active. This advantageously enables better control over the rate of color change. In particular, the odor-control active can be selected, or otherwise designed, based on the rate at which it will induce a color change.

FIG. 8B illustrates the thermoplastic bag 100 from FIG. 8A after most of the encapsulated odor control component 804 has released the encapsulated odor-control active and the color indicator 802 has changed to a second color indicating the odor-control active's release. Though FIG. 8B illustrates that the color indicator 802 has changed from a first color to a second color to indicate a release of the odor-control active, one or more embodiments involve the color indicator 802 becoming transparent to indicate the release of the odor-control active.

Because the encapsulated odor control component can be configured to release the odor-control active when exposed to malodor particles rather than requiring direct contact with the malodor source, the encapsulated odor control component can be effective even when applied to variations of the thermoplastic bag 100. For example, the encapsulated odor control component can be used with patterned variations of the thermoplastic bag 100.

Figure 9:
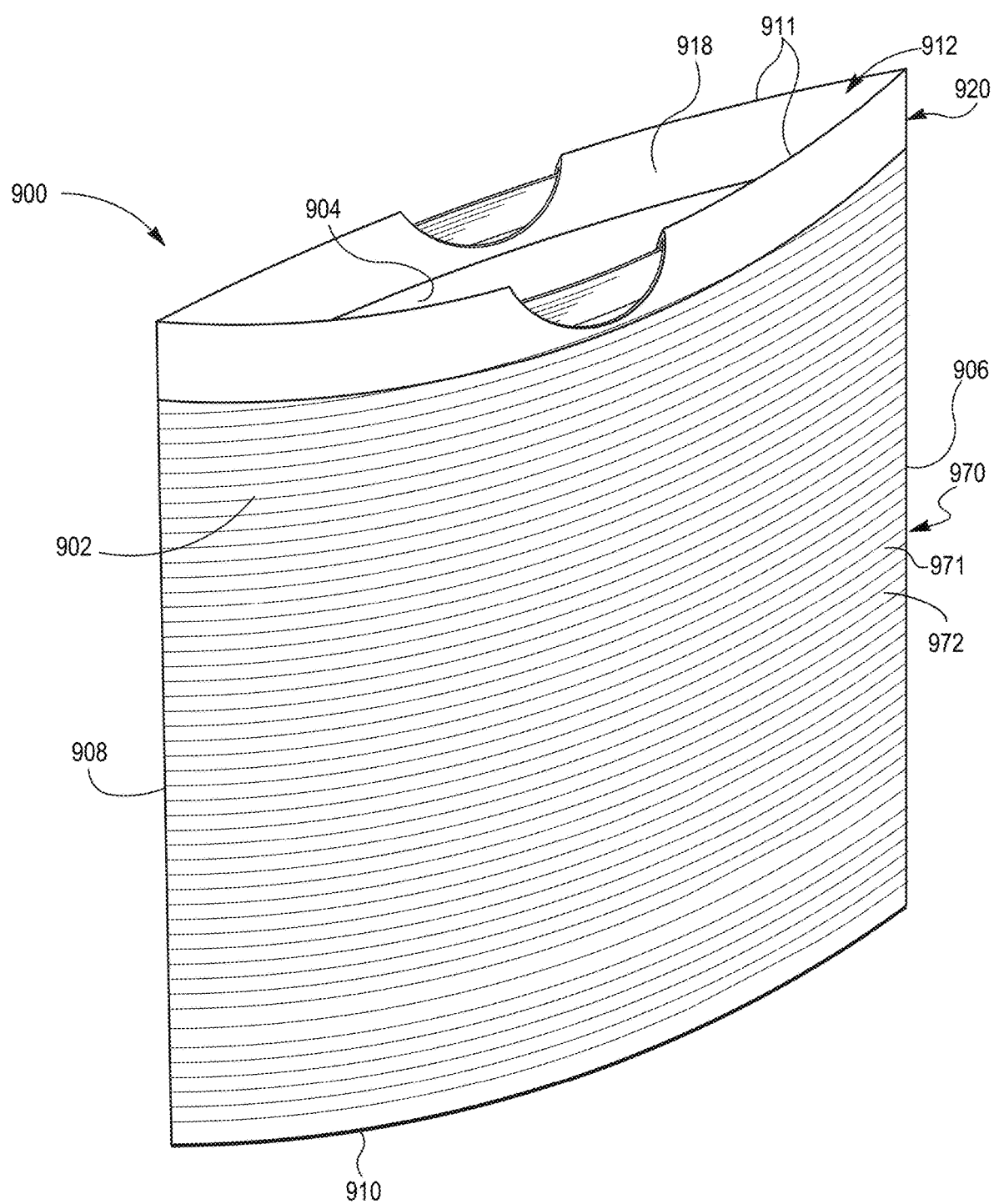
FIG. 9 illustrates a perspective view of a thermoplastic bag having a pattern in accordance with one or more embodiments.

For example, FIG. 9 illustrates a thermoplastic bag 900 similar to the thermoplastic bag 100, albeit that the sidewalls 902, 904 are incrementally stretched. In particular, the sidewalls 902, 904 include a ribbed pattern 970 of a plurality of alternating thinner (e.g., stretched) linear webs 971 and thicker linear ribs 972 that may extend across the sidewalls 902, 904 between the first side edge 906 and second side edge 908. As illustrated in FIG. 9, the webs 971 and ribs 972 may be parallel and adjacent to one another. Additionally, as illustrated in FIG. 9, the ribbed pattern 970 may extend from the bottom edge 910 toward the opening 912. To avoid interfering with the operation of the draw tape, the extension of the ribbed pattern 970 may terminate below the hems 918, 920. In alternative implementations, the ribbed pattern 970 can extend from the bottom edge 910 to the top edge 911 of each sidewall. The ribbed pattern 970 can be formed by passing the films of the sidewalls 902, 904 through a pair of transverse direction intermeshing ring rollers, such as those described in U.S. Pat. No. 9,669,595, the contents of which are hereby incorporated herein by reference in their entirety.

Figure 10:
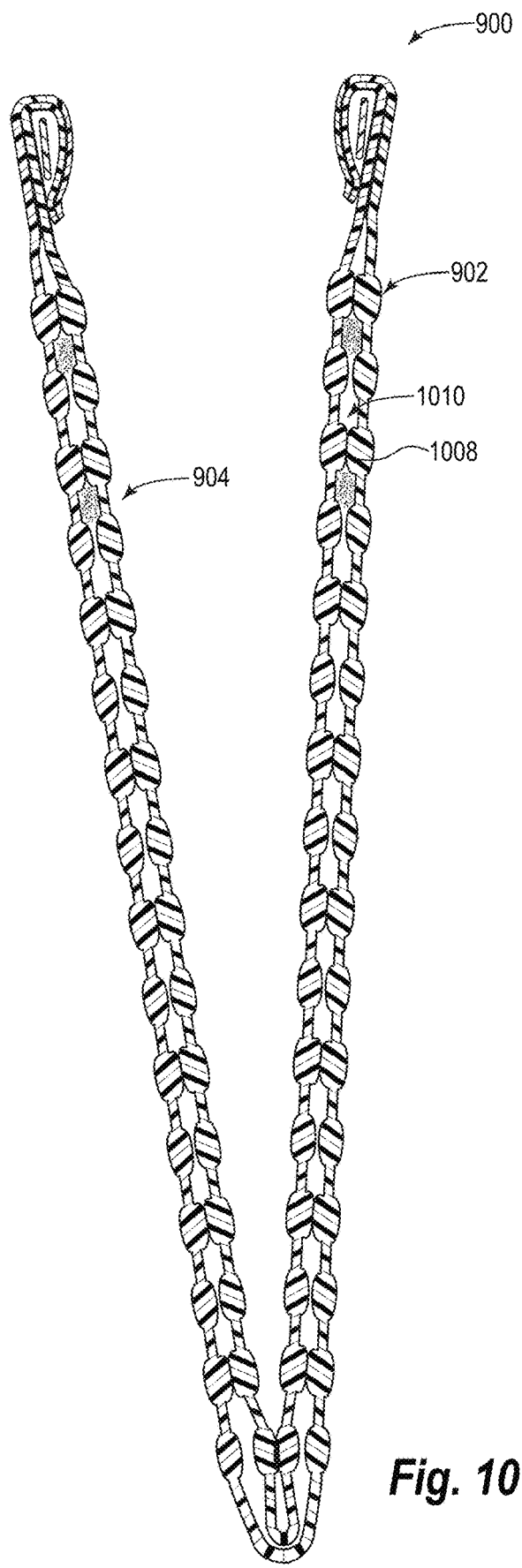
FIG. 10 illustrates a side cross-sectional view of the thermoplastic bag of FIG. 9.

FIG. 10 illustrates a side cross-sectional view of the thermoplastic bag 900 of FIG. 9. In particular, FIG. 10 shows the thermoplastic bag 900 wherein each of the sidewalls include multiple layers. As shown in FIG. 10, the multi-layer sidewalls of the thermoplastic bag 900 include bonded regions 1008 and un-bonded regions or air gaps 1010. In one or more embodiments, the un-bonded regions or air gaps 1010 are located at each sidewall where the sidewall has been stretched or cold-formed (i.e., at the location of the stretched linear webs 971 discussed with reference to FIG. 9). In some embodiments, the un-bonded regions or air gaps 1010 are located at each sidewall where the sidewall has not been stretched or cold-formed (i.e., at the location of the linear ribs 972 of FIG. 9). In some embodiments, the bonded regions 1008 may comprise less than about 30 percent of a total area of the multi-layer sidewall. Furthermore, an encapsulated odor control component may be disposed within the un-bonded regions or air gaps 1010. Disposing the encapsulated odor control component within the un-bonded regions or air gaps 1010 provides separations (e.g., distinct portions) of the encapsulated odor control component.

In still further implementations, the one or more of the layers of the thermoplastic bag can be subjected to SELFing as described in U.S. Pat. Nos. 9,669,595; 5,518,801; 6,139,185; 6,150,647; 6,394,651; 6,394,652; 6,513,975; 6,695,476; U.S. Patent Application Publication No. 2004/0134923; and U.S. Patent Application Publication No. 2006/0093766, the entire contents of each of the foregoing patents and patent applications are hereby incorporated by reference.

Figure 11:
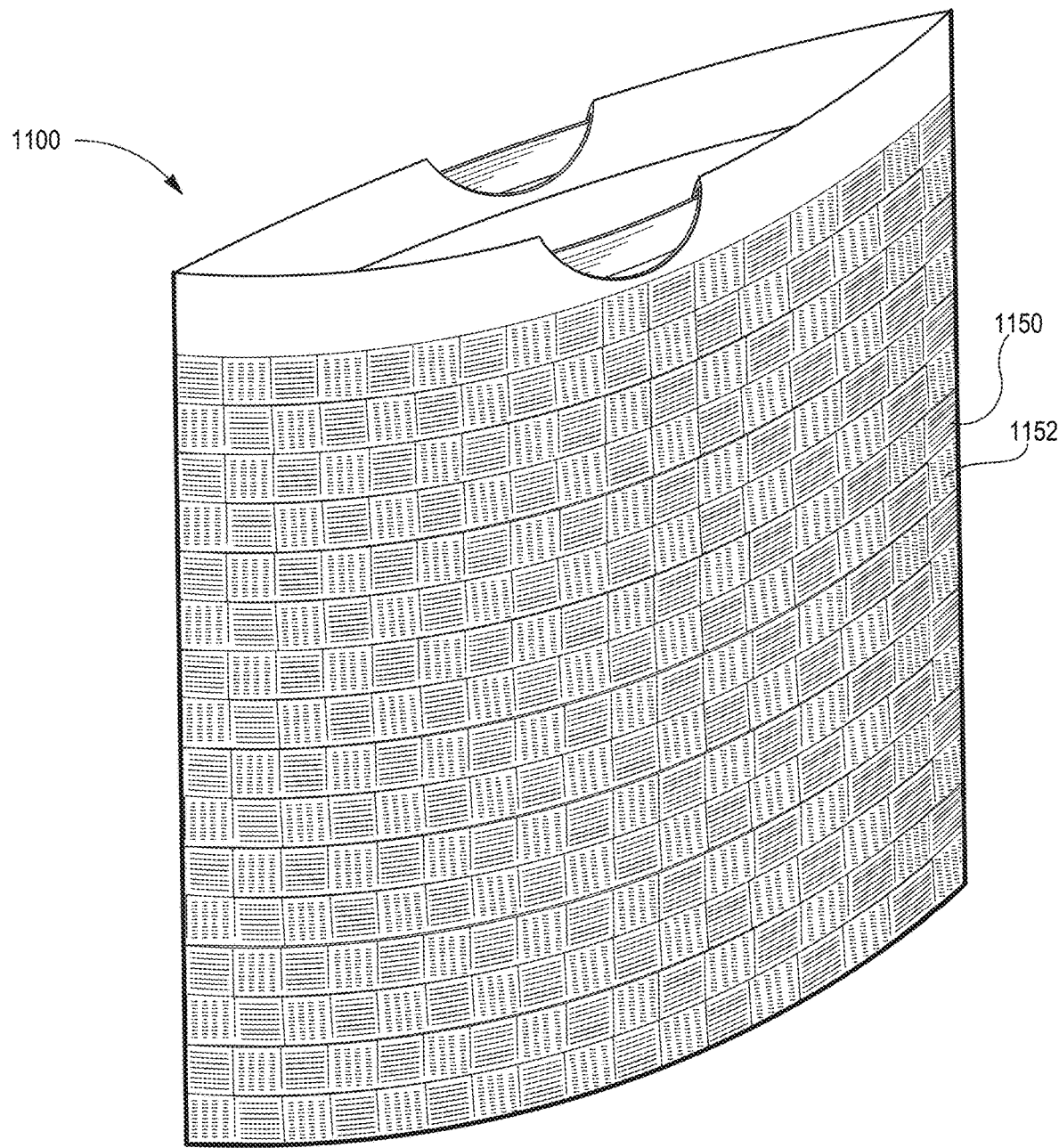
FIG. 11 illustrates a perspective view of thermoplastic bag having another pattern in accordance with one or more embodiments.

FIG. 11 illustrates another thermoplastic bag 1100 similar to the thermoplastic bag 100 albeit with sidewalls that are SELF'ed. The thermoplastic bag 1100 can include the same structure as the thermoplastic bag 900 (e.g., an encapsulated odor control component) albeit with a different pattern of intermittent bonds and thinner webs and thicker ribs. In particular, the thermoplastic bag 1100 may include a single pattern of raised like elements arranged in a checkerboard pattern. The pattern can comprise a micro pattern of raised rib-like elements 1152 and a macro pattern of raised rib-like elements 1150.

Figure 12A:
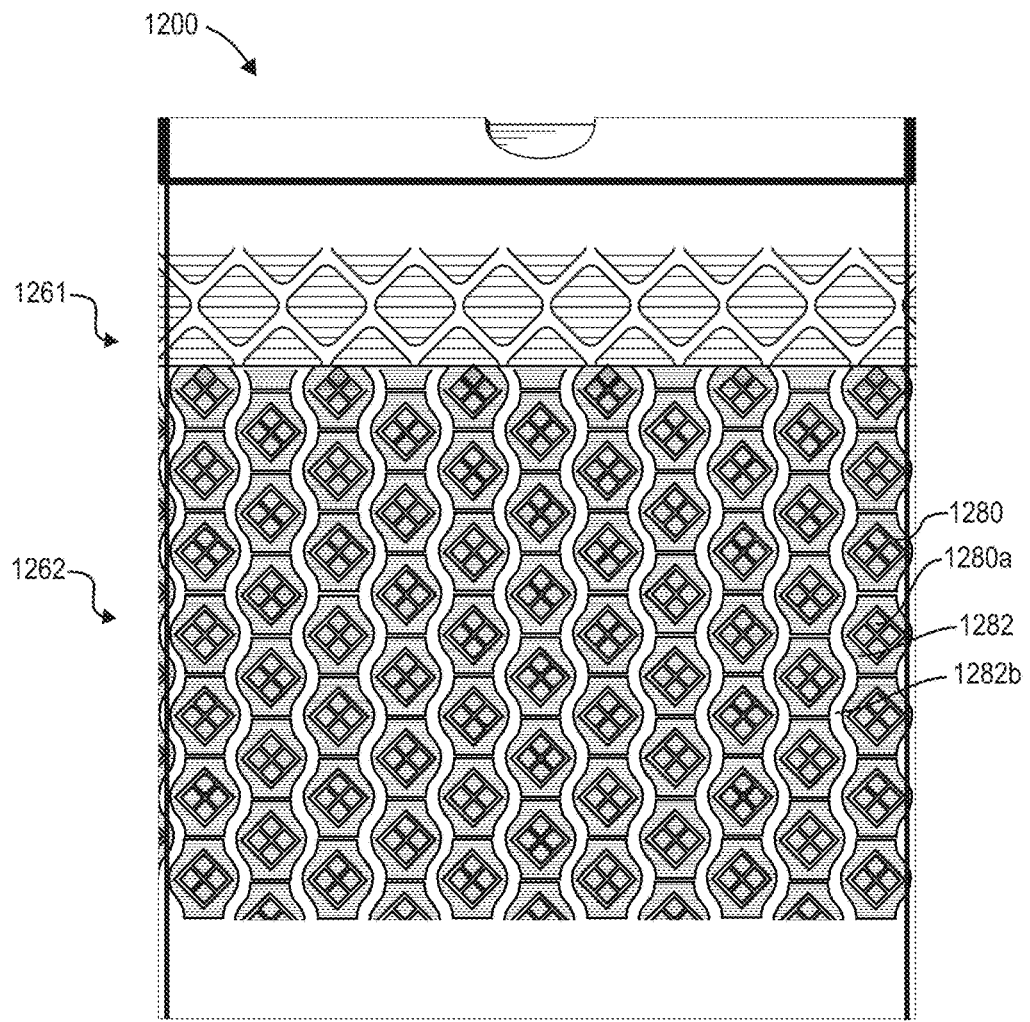
FIGS. 12A-12B illustrate a front view of a thermoplastic bag having yet another pattern in accordance with one or more embodiments.
Figure 12B:
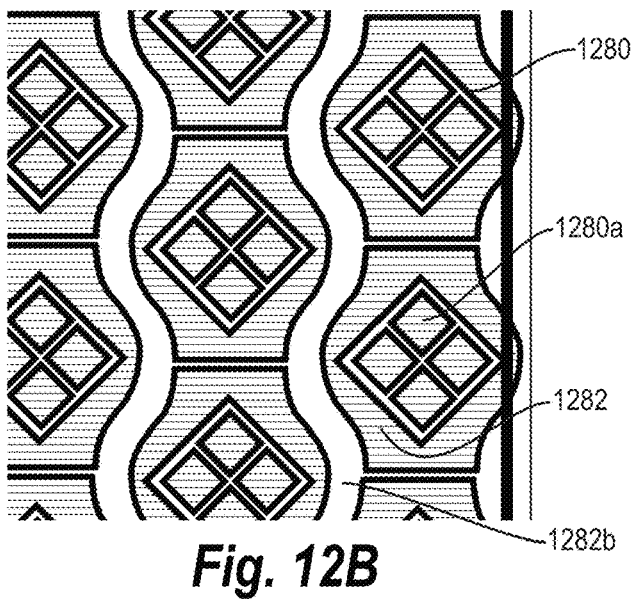

FIG. 12A shows another thermoplastic bag 1200 similar to the thermoplastic bag 100. FIG. 12B is an enlarged view of a portion of the thermoplastic bag 1200. Referring to FIGS. 12A and 12B together, one or more of the sidewalls of the thermoplastic bag 1200 have a first plurality of raised rib-like elements 1282 in a macro pattern (e.g., a bulbous pattern) and a second plurality of raised rib-like elements 1280a in a micro pattern (e.g., four diamonds) in a first middle portion 1262. As shown, the second plurality of raised rib-like elements 1280a in the micro pattern are nested within the macro patterns. Furthermore, the thermoplastic bag 1200 includes web areas 1280, 1282b. The web areas 1280, 1282b can surround the micro and the macro patterns of raised rib-like elements. The plurality of web areas 1280, 1282b comprise areas in which the first layer and the second layer are separated to form intermittent bonding between the layers (i.e., the inner bag and the outer bag). Furthermore, as shown by FIG. 12, the web areas 1282b are arranged in a sinusoidal pattern.

Additionally, FIG. 12 illustrates that the thermoplastic bags described herein can include areas with different patterns. In particular, FIG. 12 illustrates an upper potion 1261 of the thermoplastic bag 1200 including a fenced diamond pattern. The fenced diamond pattern can comprise raised-rib-like elements arranged in diamond patterns where the intersections of the sides of the diamond are rounded rather than ending in corners. The fenced diamond pattern can also comprise areas in which the first layer and the second layer are separated to form intermittent bonding between the layers (i.e., the inner bag and the outer bag).

One or more implementations of the present invention can also include methods of forming thermoplastic bags. FIGS.

13-14 and the accompanying description describe such methods. Of course, as a preliminary matter, one of ordinary skill in the art will recognize that the methods explained in detail herein can be modified. For example, various acts of the method described can be omitted or expanded, additional acts can be included, and the order of the various acts of the method described can be altered as desired.

Figure 13:
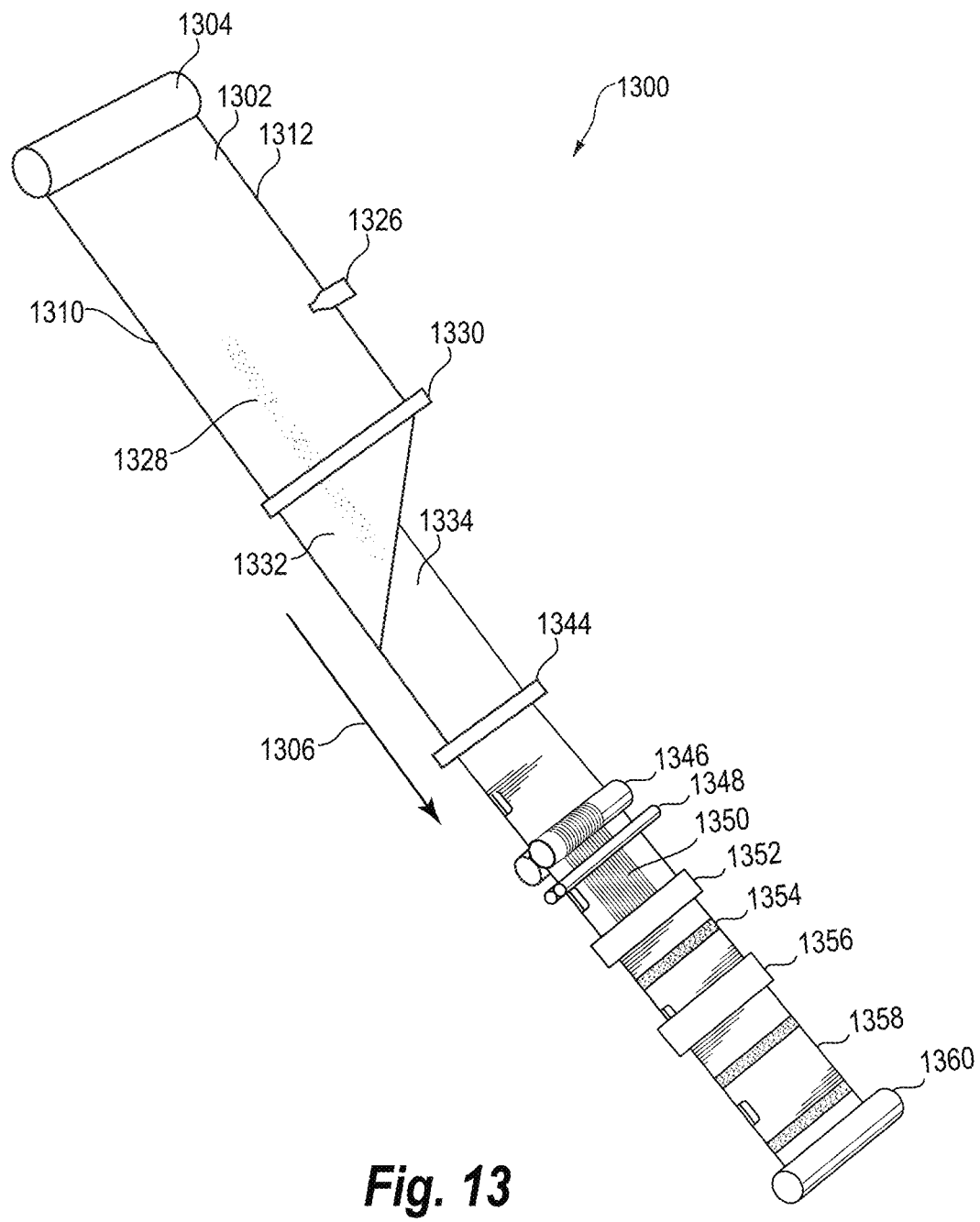
FIG. 13 illustrates a schematic diagram of a manufacturing process for producing thermoplastic bags having an odor control component in accordance with one or more embodiments.

Referring to FIG. 13, a schematic of an implementation for high-speed automated manufacturing of bags process 1300 is shown. In the illustrated implementation, the process 1300 may begin by unwinding a web 1302 of thermoplastic sheet material from a roll 1304 and advancing the web along a machine direction 1306. The unwound web 1302 may have a rectangular profile including a width that is perpendicular to the machine direction 1306 as measured between a first edge 1310 and an opposite second edge 1312. In other manufacturing environments, the process may involve extruding the web 1302 using a thermoplastic production process.

After unwinding the web 1302, the process 1300 can involve dispensing a substance 1328 containing an encapsulated odor control component using a dispenser 1326. In one or more embodiments, the substance 1328 is additionally, or alternatively, applied using a roller or a slot cast. In one or more embodiments, the substance 1328 includes a liquid application, a powder application or any other application discussed above. As mentioned above, the process 1300 can be modified so that the act of applying the substance containing the encapsulated odor control component can occur earlier or later than what is shown in FIG. 13. For example, in one or more embodiments, the substance containing 1328 containing the encapsulated odor control component (or the encapsulated odor control component itself) can be coextruded with the web 1302 using the thermoplastic production process.

Subsequently, the process 1300 can include a folding process 1330 that involves folding the web 1302 about its width and in-line with the machine direction 1306 to provide adjacent first and second folded halves 1332, 1334. The folding of the web 1302 may cause the second edge 1312 to move adjacent to the first edge 1310 such that the two edges correspond to the opened top edge of the finished bag. The mid-width portion of the web 1302 may correspond to the reinforced bottom edge portion of the finished bag which may move in parallel with the machine direction 1306. Additionally, the folded halves 1332, 1334 of the web 1302 correspond to the first and second sidewalls of the finished bag.

Additional processing steps may be applied to produce the finished bag. In particular, the process 1300 can include a draw tape insertion process 1344 that involves inserting a draw tape into the first edge 1310 and the second edge 1312 of the web 1302.

Optionally, to bond (and optionally stretch) the halves of the web, the processing equipment may include a pair of intermeshing rollers 1346 such as those described herein above. The folded halves 1332, 1334 may be advanced along the machine direction 1306 between the intermeshing rollers 1346, which may be set into rotation in opposite rotational directions to impart the resulting bonding pattern 1350. To facilitate patterning of the folded halves 1332, 1334, the intermeshing rollers 1346 may be forced or directed against each other by, for example, hydraulic actuators. The pressure at which the rollers are pressed together may be in a first range from 30 PSI (2.04 atm) to 100 PSI (6.8 atm), a second range from 60 PSI (4.08 atm) to 90 PSI (6.12 atm), and a third range from 75 PSI (5.10 atm) to 85 PSI (5.78 atm). In one or more implementations, the pressure may be about 80 PSI (5.44 atm).

In the illustrated implementation, the intermeshing rollers 1346 may be arranged so that they are co-extensive with or wider than the width of the folded halves 1332, 1334. In one or more implementations, the bonding pattern 1350 created by intermeshing rollers 1346 may extend from proximate the folded edge to the adjacent edges 1310, 1312. To avoid imparting the bonding pattern 1350 onto the portion of the folded halves 1332, 1334 that includes the draw tape, the corresponding ends of the intermeshing rollers 1346 may be smooth and without the ridges and grooves. Thus, the adjacent edges 1310, 1312 and the corresponding portion of the folded halves 1332, 1334 proximate those edges that pass between the smooth ends of the intermeshing rollers 1346 may not be imparted with the bonding pattern 1350.

The processing equipment may include pinch rollers 1348 to accommodate the width of the folded halves 1332, 1334. To produce the finished bag, the processing equipment may further process the folded halves 1332, 1334. For example, to form the parallel side edges of the finished bag, the folded halves 1332, 1334 may proceed through a sealing operation 1352 in which heat seals 1354 may be formed between the folded edge and the adjacent edges 1310, 1312. The heat seals may fuse together the adjacent folded halves 1332, 1334. The heat seals 1354 may be spaced apart along the folded halves 1332, 1334 and in conjunction with the folded outer edge may define individual bags. The heat seals 1354 may be made with a heating device, such as, a heated knife or a sealing bars as described in greater detail below. A perforating operation 1356 may perforate the heat seals 1354 with a perforating device, such as, a perforating knife so that individual bags 1358 may be separated from the web 1302. In one or more implementations, the folded halves 1332, 1334 may be folded one or more times before the folded halves 1332, 1334 may be directed through the perforating operation. The folded halves 1332, 1334 embodying the individual bags 1358 may be wound into a roll 1360 for packaging and distribution. For example, the roll 1360 may be placed in a box or a bag for sale to a customer.

In one or more implementations of the process 1300, a cutting operation may replace the perforating operation 1356. The web is directed through a cutting operation which cuts the folded halves 1332, 1334 at location into individual bags 1358 prior to winding onto a roll 1360 for packaging and distribution. For example, the roll 1360 may be placed in a box or bag for sale to a customer. The bags may be interleaved prior to winding into the roll 1360. In one or more implementations, the folded halves 1332, 1334 may be folded one or more times before the folded web is cut into individual bags. In one or more implementations, the individual bags 1358 may be positioned in a box or bag, and not onto the roll 1360.

FIG. 14 illustrates an exemplary embodiment of a manufacturing process for making multi-layer thermoplastic film (e.g., the first and second films 1440, 1442) having the encapsulated odor control component 1444 (e.g., a substance containing the encapsulated odor control component 1444) disposed therein and then producing multi-layer thermoplastic bags therefrom. According to the process 1400, a first film 1440 and a second film 1442 may be unwound from stock rolls 1402, respectively, and directed along a machine direction MD. Alternatively, the first and second films 1440, 1442 may be extruded directly from one or more extrusion towers rather than stock rolls 1402.

The encapsulated odor control component 1444 (e.g., one or more substances containing the encapsulated odor control component) may be applied to one or more of the first and second films 1440, 1442 on the inner sides of the first and second films 1440, 1442 (e.g., the sides of the first and second films 1440, 1442 that will be bonded together) prior to bonding the first and second films 1440, 1442. The encapsulated odor control component 1444 may be applied through one or more of laminating, dusting, spraying, rolling, and any other method known in the art for applying substances to films. In one or more embodiments, the encapsulated odor control component 1444 (or a substance containing the encapsulated odor control component 1444) is coextruded with the first and second films 1440, 1442.

After the encapsulated odor control component 1444 has been applied to one or more of the first and second films 1440, 1442, the first and second films 1440, 1442 may be passed between a pair of cylindrical intermeshing rollers 1406, 1408 to incrementally stretch and lightly laminate the initially separate first and second films 1440, 1442 to create un-bonded regions and bonded regions in at least one section of a multi-layer film (i.e., eventual sidewall of the multi-layer bag). The intermeshing rollers 1406, 1408 shown in FIG. 14 may have a construction similar to that of any of the intermeshing rollers described in U.S. Pat. No. 8,603,609. The rollers 1406, 1408 may be oriented such that longitudinal axes of the rollers are perpendicular to the machine direction. Additionally, the rollers 1406, 1408 may rotate about their longitudinal axes in opposite rotational directions. In some embodiments, motors may be provided to power rotation of the rollers 1406, 1408 in a controlled manner. As the first and second films 1440, 1442 pass between the pair of rollers 1406, 1408, the ridges and/or teeth of the rollers 1406, 1408 can form the multi-layer film (i.e., eventual sidewall of the multi-layer bag).

During the manufacturing process 1400, the multi-layer film can also pass through a pair of pinch rollers 1410, 1412. The pinch rollers 1410, 1412 can be appropriately arranged to grasp the multi-layer film.

A folding operation 1414 can fold the multi-layer film to produce the sidewalls of the finished bag. The folding operation 1414 can fold the multi-layer film in half along the transverse direction. In particular, the folding operation 1414 can move a first edge 1416 adjacent to the second edge 1418, thereby creating a folded edge 1420. For example, the process may include the folding operation described in U.S. Pat. No. 8,568,283, the entire contents of which are hereby incorporated by reference in their entirety. Additionally, the folding operation 1414 may form a hem at an eventual top portion of a thermoplastic film.

To produce the finished bag, the processing equipment may further process the folded multi-layer film. In particular, a draw tape operation 1422 can insert a draw tape 1446 into the first edge 1416 and the second edge 1418 of the multi-layer film. Furthermore, a sealing operation 1424 can form the parallel side edges of the finished bag by forming heat seals 1426 between adjacent portions of the folded multi-layer lightly-laminated film. Moreover, the sealing operation 1424 can seal the hem to a sidewall of the eventual thermoplastic bag. The heat seal 1426 may strongly bond adjacent layers together in the location of the heat seal 1426 so as to tightly seal the edges (e.g., produce an at least substantially water tight seal) of the finished bag. The heat seals 1426 may be spaced apart along the folded multi-layer film to provide a desired width to the finished bags. The sealing operation 1424 can form the heat seals 1426 using a heating device, such as, a heated knife.

A perforating operation 1428 may form a perforation 1430 in the heat seals 1426 using a perforating device, such as, a perforating knife. The perforations 1430 in conjunction with the folded outer edge 1420 can define individual bags 1448 that may be separated from the multi-layer film. A roll 1432 can wind the multi-layer lightly-laminated film embodying the finished individual bags 1448 for packaging and distribution. For example, the roll 1432 may be placed into a box or bag for sale to a customer.

In still further implementations, the folded multi-layer lightly-laminated film may be cut into individual bags along the heat seals 1426 by a cutting operation. In another implementation, the folded multi-layer lightly-laminated film may be folded one or more times prior to the cutting operation. In yet another implementation, the side sealing operation 1424 may be combined with the cutting and/or perforation operations 1428.

In further embodiments, the hem of the thermoplastic bag may be ring rolled and/or SELF'd to form a pattern in the hem. Moreover, the hem of the thermoplastic bag may be ring rolled and/or SELF'd prior to being folded into a hem shape and/or after being folded into a hem shape.

One will appreciate in view of the disclosure herein that the process 1400 described in relation to FIG. 14 can be modified to omit or expanded acts, or vary the order of the various acts as desired. In particular, the process 1400 can involve placing or applying an odor control component such that the odor control component is positioned in or around the hem as described below.

The present disclosure may be embodied in other specific forms without departing from its spirit or essential characteristics. For example, the illustrated and described implementations involve non-continuous (i.e., discontinuous or partially discontinuous lamination) to provide the weak bonds. In alternative implementations, the lamination may be continuous. For example, multi film layers could be coextruded so that the layers have a bond strength that provides for delamination prior to film failure to provide similar benefits to those described above. Thus, the described embodiments are to be considered in all respects only as illustrative and not restrictive. The scope of the disclosure is, therefore, indicated by the appended claims rather than by the foregoing description. All changes that come within the meaning and range of equivalency of the claims are to be embraced within their scope.

What is claimed is:

1. A film, comprising:
   a first layer of thermoplastic material; and
   an encapsulated odor control component comprising an odor-control active encapsulated within an odor-control encapsulant, wherein the odor-control encapsulant comprises a crystalline lattice composed of basic material that breaks down when exposed to a volatile fatty acid due to acid-base reactions to cause a change to a structure of the odor-control encapsulant thereby releasing the odor-control active.

2. The film of claim 1, further comprising a second encapsulated odor control component comprising a second odor-control active encapsulated within a second odor-control encapsulant, wherein the second encapsulated odor control component is configured to release the second odor-control active when exposed to malodor particles other than the volatile fatty acid.

3. The film of claim 1, further comprising a second non-encapsulated odor control component.

4. The film of claim 1, wherein the encapsulated odor control component is disposed as a pattern onto a surface of the first layer of thermoplastic material.

5. The film of claim 1, wherein the encapsulated odor control component is disposed to cover a surface of the first layer of thermoplastic material.

6. The film of claim 1, wherein the encapsulated odor control component is disposed within a hem of the first layer of thermoplastic material.

7. The film of claim 1, further comprising a second layer of thermoplastic material adjacent to the first layer of thermoplastic material, wherein the encapsulated odor control component is disposed between the first layer of thermoplastic material and the second layer of thermoplastic material.

8. The film of claim 1, wherein the odor-control active comprises at least one of:
   an odor neutralizing agent;
   an absorptive agent;
   an adsorptive agent;
   an antimicrobial agent; or
   a fragrance.

9. The film of claim 1, further comprising a color indicator configured to change from a first color to a second color, wherein a rate of change from the first color to the second color can be controlled based on one or more of a chemistry of the odor-control active or a concentration of the odor-control active.

10. The film of claim 1, further comprising at least one of a powder application or a liquid application, wherein the at least one of the powder application or the liquid application comprises the encapsulated odor control component.

11. A thermoplastic bag, comprising:
    a first sidewall;
    a second sidewall opposite the first sidewall and joined with the first sidewall along a first side edge, an opposite second side edge, and a bottom edge; and
    an encapsulated odor control component comprising an odor-control active encapsulated within an odor-control encapsulant, wherein the odor-control encapsulant comprises a matrix of polymer chains encapsulating the odor-control active and an additional material that reacts with malodor, causing walls of the matrix to relax to change a structure of the odor-control encapsulant thereby releasing the odor-control active.

12. The thermoplastic bag of claim 11, wherein the malodor causing the walls of the matrix to relax and release the odor-control active comprises a first malodor; and
    further comprising a second encapsulated odor control component comprising a second odor-control active encapsulated within a second odor-control encapsulant, wherein the second encapsulated odor control component is configured to release the second odor-control active when exposed to a second malodor that differs from the first malodor.

13. The thermoplastic bag of claim 11, wherein the encapsulated odor control component is embedded as an additive into at least one of the first sidewall or the second sidewall during an extrusion process.

14. The thermoplastic bag of claim 11, wherein at least one of the first sidewall and the second sidewall comprises a first film of thermoplastic material and a second film of thermoplastic material, and the encapsulated odor control component is disposed between the first film and the second film of thermoplastic material.

15. The thermoplastic bag of claim 11, further comprising a color indicator configured to change from a first color to a second color, wherein a rate of change from the first color to the second color can be controlled based on a chemical structure of the odor-control active.

16. The film of claim 2, wherein the second odor-control encapsulant of the second encapsulated odor control component comprises a flexible matrix that encapsulates the second odor-control active and another material that reacts with the malodor particles, causing walls of the flexible matrix to relax and release the second odor-control active.

17. The film of claim 16, wherein the flexible matrix of the second odor-control encapsulant comprises a matrix made of polymer chains.

18. The film of claim 2, wherein the second odor-control encapsulant of the second encapsulated odor control component comprises magnesium intercalated bleach.

19. The thermoplastic bag of claim 12, wherein the second odor-control encapsulant of the second encapsulated odor control component comprises a crystalline lattice composed of basic material that breaks down when exposed to the second malodor thereby releasing the odor-control active.

20. The thermoplastic bag of claim 11, wherein the additional material encapsulated by the matrix of polymer chains comprises a transition metal particle.

* * * * *